(12) United States Patent
Chin et al.

(10) Patent No.: US 9,072,894 B2
(45) Date of Patent: Jul. 7, 2015

(54) METHOD AND APPARATUS FOR RADIOABLATION OF REGULAR TARGETS SUCH AS SYMPATHETIC NERVES

(75) Inventors: Robert K. Chin, Chicago, IL (US); Matthew Thomas Wheeler, Palo Alto, CA (US); Peter G. Maxim, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 384 days.

(21) Appl. No.: 13/522,950

(22) PCT Filed: Jan. 14, 2011

(86) PCT No.: PCT/US2011/021404
§ 371 (c)(1),
(2), (4) Date: Jul. 18, 2012

(87) PCT Pub. No.: WO2011/088399
PCT Pub. Date: Jul. 21, 2011

(65) Prior Publication Data
US 2012/0294424 A1    Nov. 22, 2012

Related U.S. Application Data

(60) Provisional application No. 61/295,767, filed on Jan. 18, 2010.

(51) Int. Cl.
*A61N 5/10* (2006.01)
*A61N 5/01* (2006.01)
*A61B 18/00* (2006.01)

(52) U.S. Cl.
CPC ............. *A61N 5/1042* (2013.01); *A61N 5/01* (2013.01); *A61N 5/1081* (2013.01); *A61B 2018/00434* (2013.01)

(58) Field of Classification Search
CPC ................. A61N 5/01; A61N 5/1081; A61B 2018/00434
USPC ........................................ 378/64, 65
See application file for complete search history.

(56) References Cited

U.S. PATENT DOCUMENTS 5,150,394 A * 9/1992 Karellas ............... 378/62
5,574,763 A * 11/1996 Dehner ................ 378/17

(Continued)

OTHER PUBLICATIONS

USISA, "International Search Report and Written Opinion for the corresponding PCT application PCT/US 11/21404", Apr. 8, 2011, pp. 1-13, Publisher: ISA, Published in: Alexandria, Virginia / US.

*Primary Examiner* — Michael Maskell
(74) *Attorney, Agent, or Firm* — Evans & Molinelli PLLC; Engene J. Molinelli

(57) ABSTRACT

Techniques for radioablation of sympathetic nerves include positioning a subject on a support in view of a volume imaging system and an ionizing radiation source; and collecting volume image data. Location of a treatment portion of a sympathetic nerve in the subject is determined based on the volume image data. Movement of the source is determined to apply a therapeutic radiation dose to the treatment portion based on the location of the treatment portion and relative location of the source to the volume imaging system. The source is operated to deliver the therapeutic radiation dose. An apparatus includes a mounting structure, an X-ray source and a shield. The source produces an X-ray beam with photon energy above one million electron volts (MeV) and not above six MeV. The shield is mounted in opposition to the source to block the X-ray beam with photon energies not greater than about six MeV.

19 Claims, 16 Drawing Sheets

(56) References Cited

U.S. PATENT DOCUMENTS

| | | | |
|---|---|---|---|
| 8,295,912 B2* | 10/2012 | Gertner | 600/426 |
| 8,462,912 B2* | 6/2013 | O'Connor et al. | 378/68 |
| 2007/0265687 A1* | 11/2007 | Deem et al. | 607/72 |
| 2009/0149735 A1* | 6/2009 | Fallone et al. | 600/411 |
| 2010/0002837 A1* | 1/2010 | Gertner et al. | 378/65 |
| 2011/0200171 A1* | 8/2011 | Beetel et al. | 378/65 |

* cited by examiner

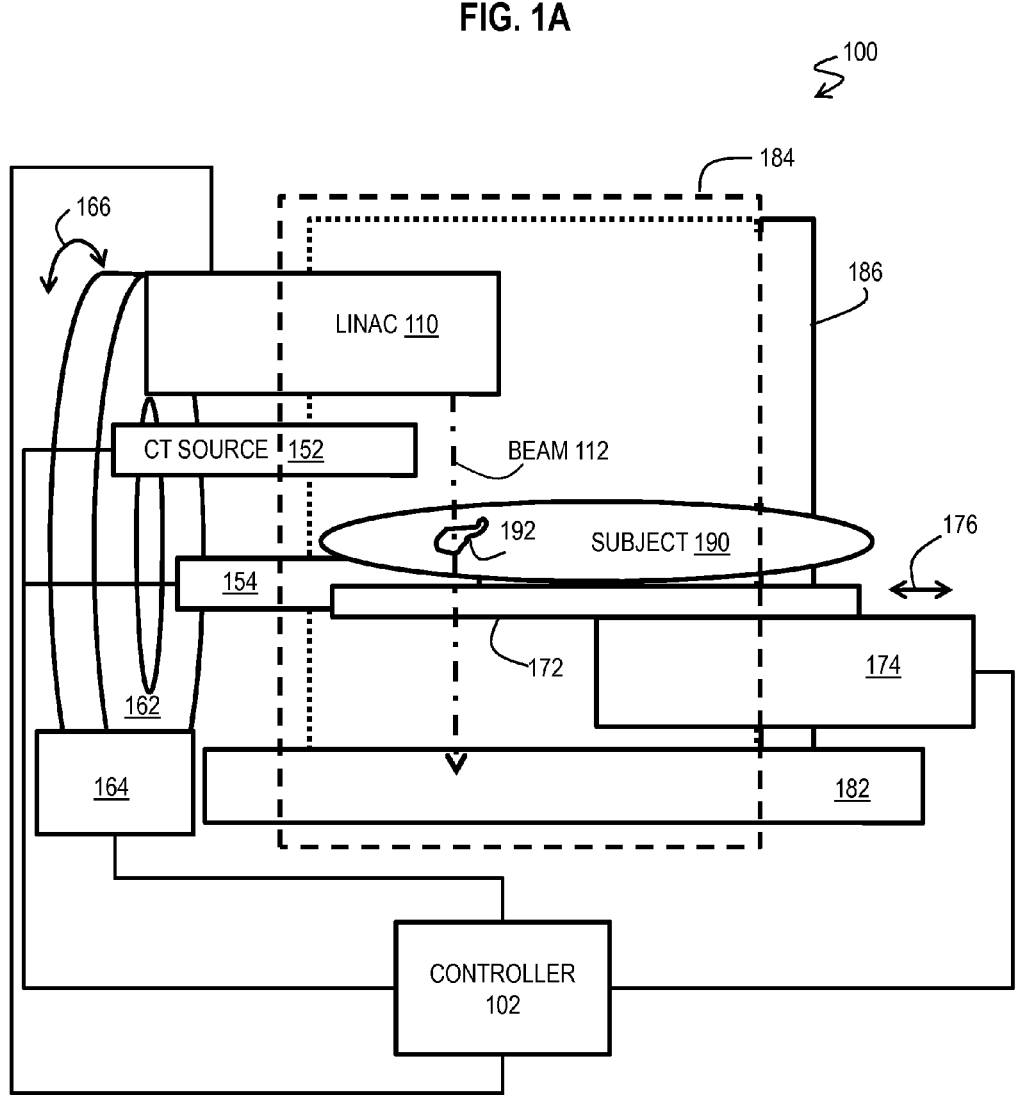

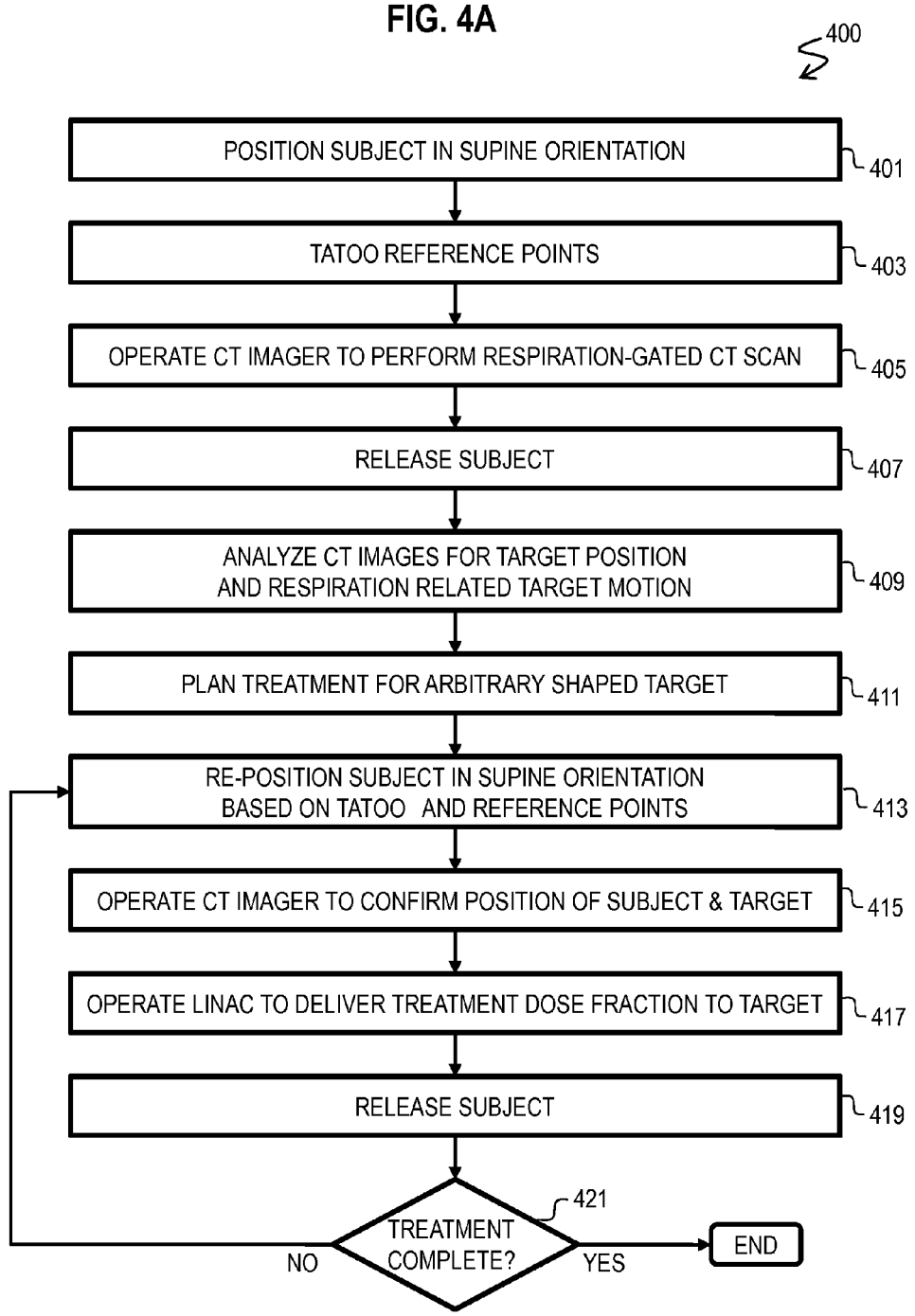

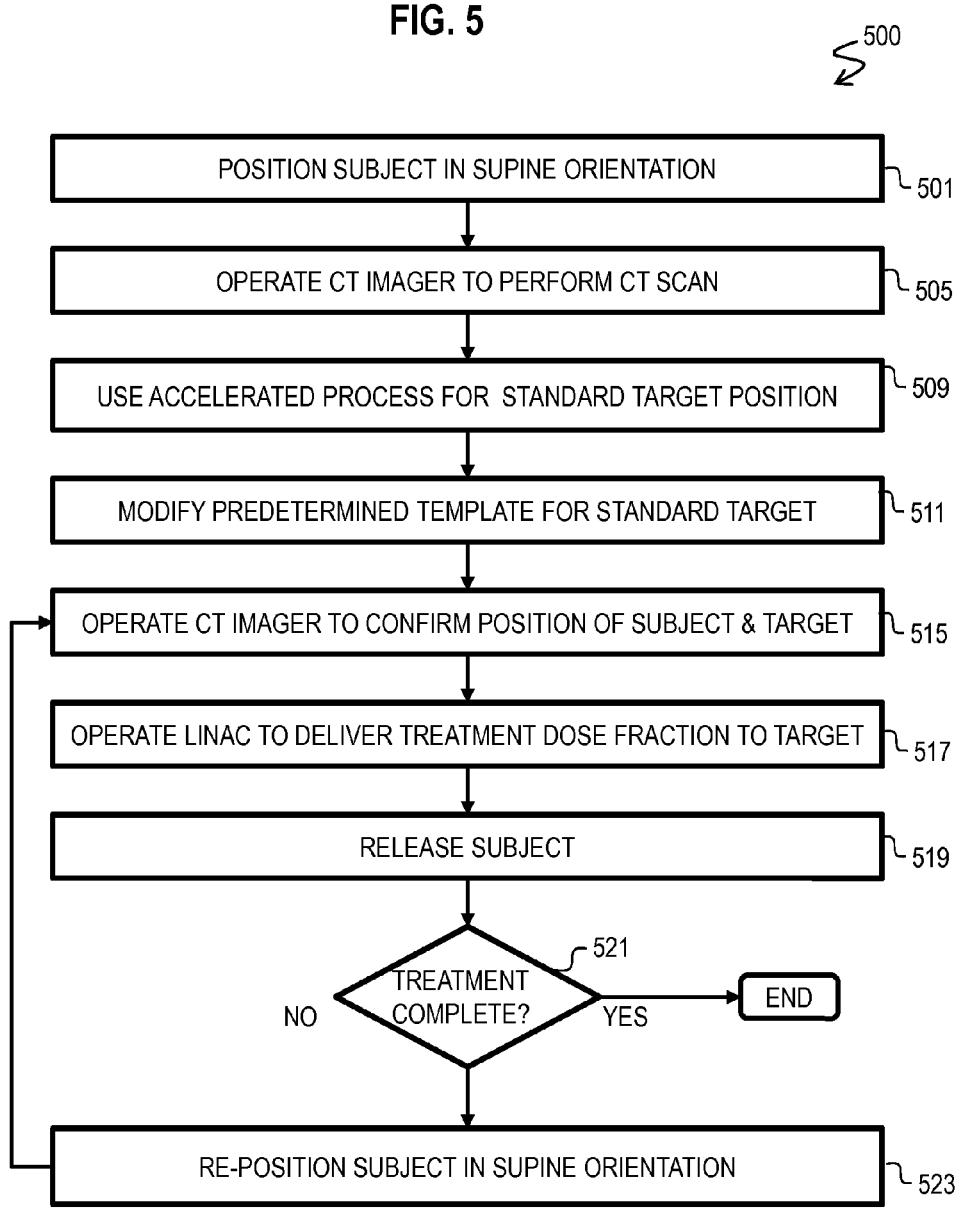

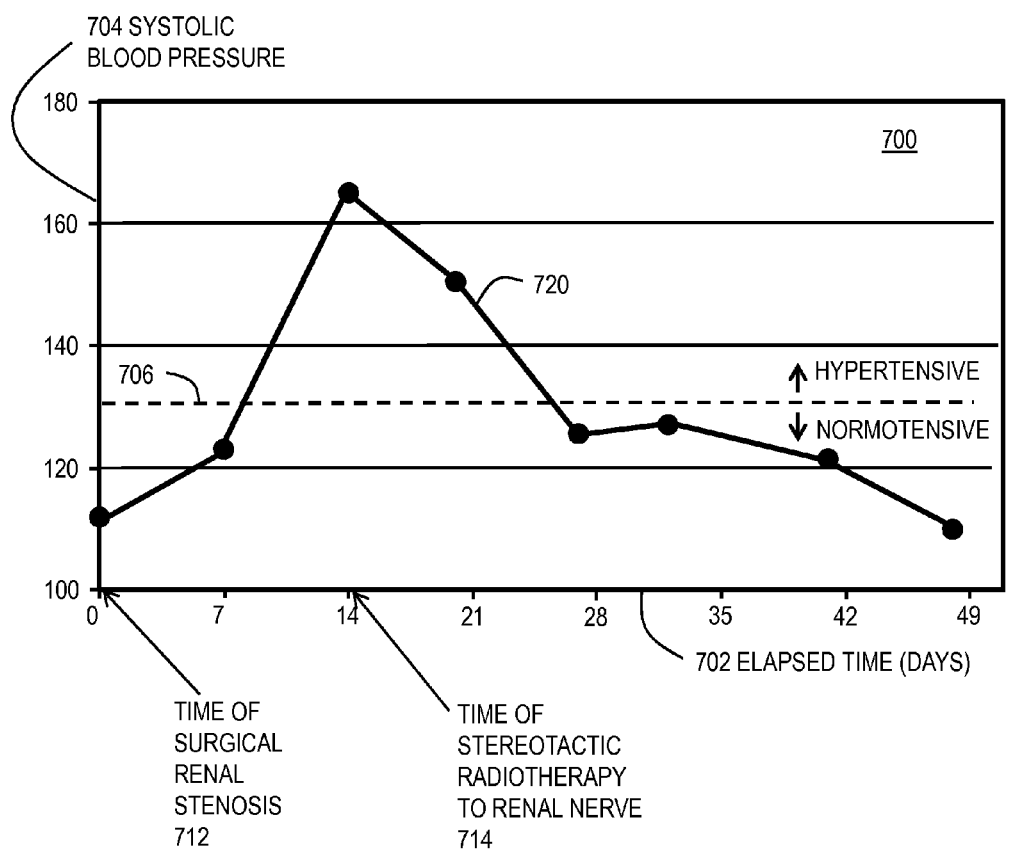

METHOD AND APPARATUS FOR RADIOABLATION OF REGULAR TARGETS SUCH AS SYMPATHETIC NERVES

CROSS-REFERENCE TO RELATED APPLICATIONS

This application claims benefit of Provisional Appln. 61/295,767, filed Jan. 18, 2010, the entire contents of which are hereby incorporated by reference as if fully set forth herein, under 35 U.S.C. §119(e).

STATEMENT OF GOVERNMENTAL INTEREST

This invention was made with Government support under Contract No. 5TL1RR025742-02 awarded by the National Institutes of Health. The Government has certain rights in the invention.

BACKGROUND

Hypertension is a significant health care issue, estimated to affect 30-40% of adults in the developed world and increasing in prevalence in the developing countries. Despite the numerous single agent and combination therapies available, large swathes of patients ultimately prove unresponsive (refractory) to established therapies. Some of these patients are unable to adhere to a life-long course of drug therapy for a disease that is asymptomatic until its devastating conclusion. Others cases are refractory despite the best attempts of both patients and physicians. Both classes of patients are at high risk for end-organ damage leading to morbidity and mortality from their hypertension, and both would benefit from a procedure that 1) eliminates the need for lifelong pharmacotherapy, and 2) radically departs from pathways targeted by established anti-hypertensive therapy. This is especially true in populations for whom control of hypertension has clear and dramatic effects on survival. In dialysis-dependent patients, for example, control of hypertension reduces mortality risk by half.

The renal sympathetic nervous system, including both afferent and efferent fibers, runs adjacent to the renal artery. These fibers are critical for the initiation and maintenance of systemic hypertension. In both animal models and small clinical series, surgical methods of renal sympathetic removal of nerves (denervation), often via removal of the entire kidney (full nephrectomy), led to a dramatic lowering of blood pressure in patients who were otherwise refractory to all existing therapies. The risks in morbidity, mortality, and long term complications associated with a full nephrectomy, however, have prevented this therapy from wide adoption.

SOME EXAMPLE EMBODIMENTS

Therefore, there is a need for denervation of sympathetic nerves, such as a non-invasive procedure, which does not suffer the disadvantage of previous approaches. For example, there is a need for ablating dysfunctional sympathetic nerves using high dose, precisely applied radiation (called radioablation, herein). In various embodiments, radioablation is used for treatment of the renal sympathetic nerves for amelioration of refractory hypertension, and treatment of the thoracic sympathetic nerves for prevention of ventricular arrhythmia. While these treatments can be carried out on existing clinical linear accelerators, sympathetic nerve targets are superficial, these targets are uniform in size and shape, and the potential patient population is large. Thus, in some embodiments, a dedicated linear accelerator system for targeting sympathetic nerve targets and other regular targets is vastly simplified, without sacrificing precision of treatment.

According to a first set of embodiments, a method includes positioning a subject on a support in view of a volume imaging system and an ionizing radiation source. Volume image data is collected for the subject based on the volume imaging system. Location of a treatment portion of a sympathetic nerve in the subject is determined based at least in part on the volume image data. Movement of the ionizing radiation source to apply a therapeutic radiation dose to the treatment portion of the sympathetic nerve is determined based at least in part on the location of the treatment portion of the sympathetic nerve and relative location of the ionizing radiation source to the volume imaging system. The ionizing radiation source is operated to deliver the therapeutic radiation dose to the treatment portion of the sympathetic nerve.

According to a second set of embodiments, an apparatus includes a mounting structure, an X-ray source and a shield. The X-ray source is mounted to the mounting structure; and the X-ray source produces an X-ray beam that includes photons with photon energy above 1 million electron volts and does not include photons with photon energy above six million electron volts. The shield is mounted on the mounting structure in opposition to the X-ray source to block the X-ray beam from the X-ray source for photons with photon energies not greater than about six million electron volts.

In some embodiments of the second set, the X-ray source excludes a multi-leaf collimator and further comprises at least one shaping cone configured to target at least one sympathetic nerve in a living body.

In some embodiments of the second set, the apparatus includes a volume imaging system mounted on the mounting structure in a predetermined relationship to the X-ray source.

In some embodiments of the second set, the apparatus includes a subject support, wherein the subject support is disposed between the X-ray source and the shield in rotatable orientation relative to the mounting structure. In some of these embodiments, the subject support is a chair that supports a subject in a seated position.

According to various other sets of embodiments, a computer-readable storage medium or an apparatus is configured to perform one or more steps of the above method.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings, in which:

FIG. 1A is a block diagram that illustrates an example system for radioablation of a sympathetic nerve, according to one embodiment;

FIG. 4A is a flowchart that illustrates an example process for radioablation of a arbitrary target using the system of FIG. 1A, according to one embodiment;

FIG. 5 is a flowchart that illustrates an example process for radioablation of a sympathetic nerve using the system of FIG. 1A, according to one embodiment;

FIG. 7C is a graph that illustrates example results of radioablation of a renal sympathetic nerve, according to an embodiment;

DETAILED DESCRIPTION OF EXAMPLE EMBODIMENTS

Figure 1B:
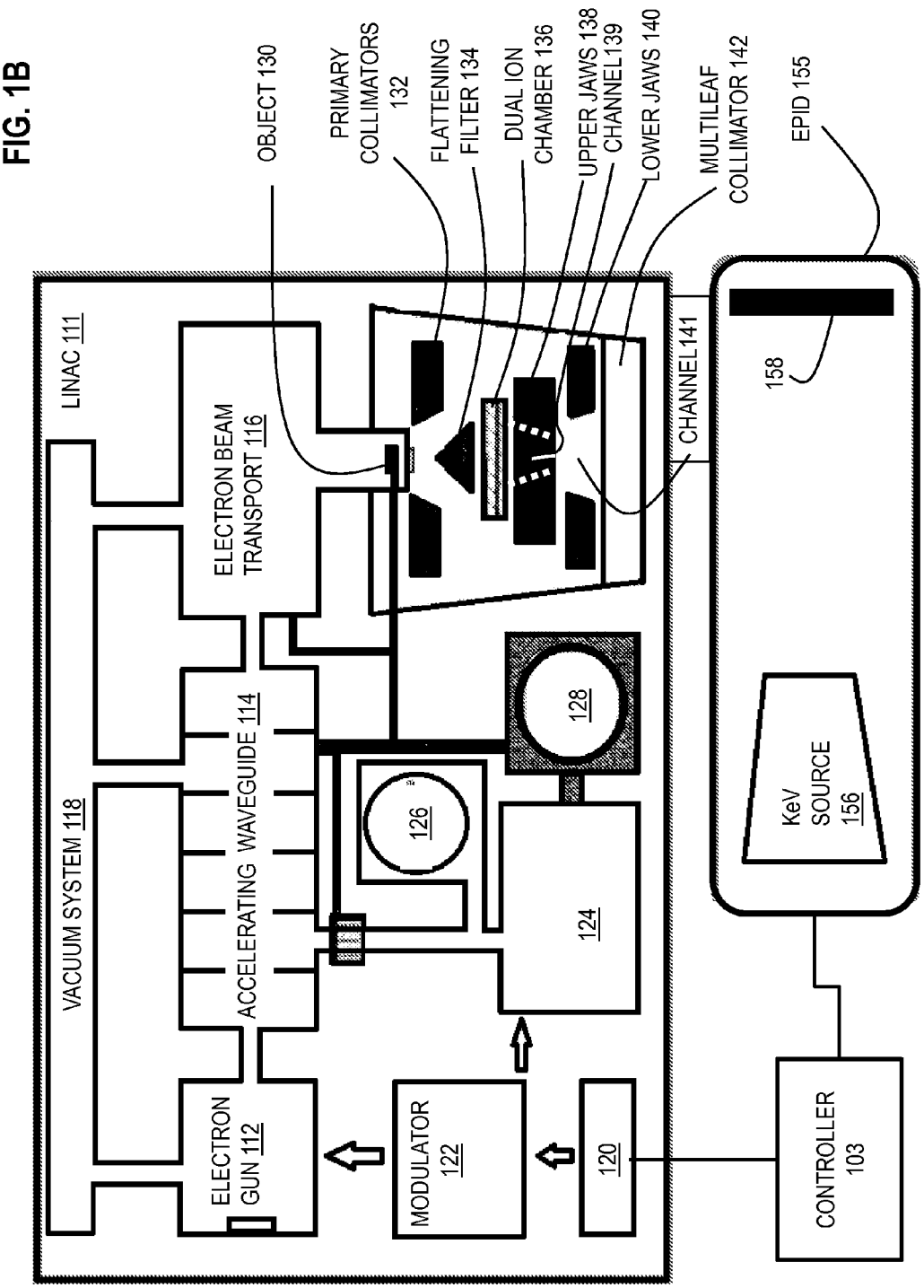
FIG. 1B is a block diagram that illustrates an example linear accelerator for the system of FIG. 1A, according to one embodiment.

A method, apparatus, and software are disclosed for radioablation of portions of sympathetic nerves. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Although several embodiments of the invention are discussed with respect to treatment of renal sympathetic nerves with an X-ray source that includes an electron gun, embodiments of the invention are not limited to this context. It is explicitly anticipated that other sympathetic nerves and similar regularly-shaped, shallow structures may also be targeted, such as a thoracic sympathetic nerve associated with arrhythmia, Pain syndromes; hyperhidrosis; excessive facial flushing; dysautonomia, for example with spinal cord or brain injury; postural dysregulation; asthma and chronic obstructive pulmonary disease mediated by thoracic and bronchiolar sympathetic nerves; nutcracker esophagus and other disorders of gut motility; gastroparesis; abnormalities in pupil function or atrigeminal neuralgia, arteriovenous malformations, brain lesions (metastatic lesions to the brain, meningiomas, etc), boost for head and neck cancer, acoustic neuromas, chordomas, metastatic lesions to the spine, early primary lung lesions, metastatic lesions to the liver. It is also expressly anticipated that other types of ionizing radiation may be produced by the linear accelerators, such as gamma rays from Cobalt 60.

FIG. 1A is a block diagram that illustrates an example system 100 for radioablation of a sympathetic nerve, according to one embodiment. This system is representative of currently available, but very expensive equipment that is used in some embodiments. The system 100 comprises a volume imaging system that includes a computer tomography (CT) source 152 and CT detector 154 (collectively referenced hereinafter as CT system 150), as well as a linear accelerator (LINAC) 110 for producing X-rays as the ionizing radiation that, in sufficient dosages, will ablate (remove one or more functions of) living tissue in a subject. One or both of the LINAC 110 and CT system 150 are mounted on a rotating gantry or ring that includes a stand 164 and a rotating portion 162 that rotates within a vertical plane (collectively referenced hereinafter as gantry 160). For simplicity both the LINAC 110 and CT system 150 are depicted on the same gantry 160; but, in some embodiments, they are on different gantries or other rotating support structures, or on one more different structures capable of both vertical plane rotation and displacement, such as a robotic arm. Thus, in some embodiments, an apparatus 100 includes a volume imaging system mounted on a mounting structure in a predetermined relationship to the X-ray source.

Ionizing radiation causes electrons in atoms in a material to break free of their atoms, thus causing ions. Thus it requires photons with enough energy to free these electrons. The energy of individual photons is proportional to the frequency of the radiation by Planck's constant (and inversely proportional to the wavelength). The energy of a photon is expressed in terms of election volts (eV), the amount of energy imparted to one electron by an electric field of one volt. Particles or photons with energies above a few electron volts (eV) are ionizing. X-rays have wavelengths in the range of about 0.01 to 10 nanometers (nm, 1 nm=$10^{-9}$ meters), corresponding to frequencies in the range of about $3 \times 10^{16}$ hertz (Hz) to $3 \times 10^{19}$ Hz and photon energies in the range from about 120 eV to 120 kilo-electron volts (KeV, 1 KeV=$10^3$ eV) and above to tens of mega electron volts (MeV, 1 MeV=$10^6$ eV).

The number of photons impinging within a period of time (called the intensity or energy flux) determines how much of the material will be ionized. Dose indicates the time integrated amount of ionizing energy absorbed by a material. Dose is expressed in the units of grays (Gy), where 1 Gy=1 joule/kilogram, and represents the amount of radiation required to deposit 1 joule of energy in 1 kilogram of any kind of matter.

The system 100 also includes a subject support structure that includes a stationary base 174 and a translating support 172 (collectively referenced hereinafter as subject support structure 170). The system 100 further includes shielding structures to block ionizing radiation emitted from the LINAC 110, such as floor shielding panel 182, and front and back wall shielding panels 184 and 186, respectively (collectively referenced hereinafter as shielding structures 180). Thus, this apparatus 100 includes a subject support 170, wherein the subject support 170 is disposed between the X-ray source (e.g., LINAC 110) and the shield (e.g., panel 182) in rotatable orientation relative to the mounting structure (floor) because the LINAC 110 rotates with the rotating portion 162.

Operation of the LINAC 110, CT system 150, gantry 160 and subject support structure 170 are coordinated by a controller 102. In some embodiments the controller includes, or is included in, one or more programmed computers or chip sets, or some combination, as described in more detail below with reference to FIG. 8 and FIG. 9. Though controller 102 is depicted as connected by wires to LINAC 110, CT system 150 and subject support structure 170 for purposes of illustration, in other embodiments, one or more connections are wireless communication channels. While subject 190 is also depicted in FIG. 1A to illustrate the operation of the system 100, the subject 190 is not part of the system 100.

The system 100 is used routinely to ablate, non-invasively, a target in subject 190, such as irregularly shaped target 192 like a tumor. The target 192 size, shape and location in the subject 190 are determined by human analyst using volume imaging data from the CT system 150. The CT source 152 passes a low photon energy beam at a dose that does not cause damaging ionization through the subject at multiple different angles in the vertical plane and at multiple positions of subject 190 on translating support 172. The different angles are obtained by rotating the rotating portion 162 in the vertical plane, as indicted by rotation direction arrow 166. The different horizontal positions are obtained by translating the translating support 172 in a horizontal direction indicated by arrow 176, which is nearly or precisely perpendicular to the vertical plane of the gantry rotation 166. Each beam is received by a two-dimension array of sensors in the detector 154. Computed tomography is used, as is well known in the art, to deduce a volume image of the insides of at least a portion of subject 190 from the multiple two-dimensional images provided by detector 154. In various embodiments, controller 102 performs the computer tomography calculations, or exports data to a separate device on a network, which performs the calculations and returns the volume imagery data. One or more analysts, such as medical radiologists or physicians, interpret the images to deduce the size, shape and location of the target 192. This determination by the analysts can take hours over the course of several days. The analysts then provide the boundary of the target 192, which is converted by the controller 102 into the coordinate space used by the system 100.

Once the size, shape and location of the target 192 is known, and the treatment plan is created and approved by the physician, the LINAC 110 is operated to emit an ionizing beam 112 of sufficiently high photon energy that repeated exposure to the beam 112 cause ablation of exposed tissue. A solution is determined that indicates how to operate the LINAC 110 to repeatedly expose tissue inside the target 192 to the beam 112 while minimizing the exposure of tissue in the subject 190 outside the target 192. The LINAC 110 is operated by controlling the intensity or photon energy or both of the emitted beam 112, and rotating the LINAC 110 in the vertical plane by virtue of rotation of rotating portion 162 of gantry 160 to attack the target from different vertical angles, and moving the subject horizontally by virtue of the translating support 172 to attack different parts of the target. For example, a dosimetrist or physicist computes the optimal beam energies, beam angles, and beam shapes to deliver the prescribed dose to the prescribed target, with minimal exposure of adjacent tissues. Adjacent organs and structures at high risk are often contoured and identified, and have maximal tolerable doses prescribed to aid in planning. Existing computer algorithms are known to deduce the solution, called the treatment plan, for existing LINACs, rotations and translations. Once the solution is determined, the subject is re-positioned on the support structure 170, as described in more detail below, and the controller 102 operates the LINAC 110, gantry 160, and support structure 170 according to the solution. In some embodiments, using a rotating gantry, the target 192 is centered at the axis of rotation of the gantry. In some embodiments, the LINAC 110, at least, is disposed on a robotic arm so that more complex movements in the vertical plane can be accomplished to compensate for a non-centered target 192.

The LINAC 110 of system 110 is designed to output a wide range of photon energy values and intensities for beams of widely varying beam widths to allow a very general target to be ablated. Such design adds to the cost and complexity of both the LINAC 110 and the shielding 180.

FIG. 1B is a block diagram that illustrates an example linear accelerator (LINAC) 111 for the system of FIG. 1A, according to one embodiment. This shows the typical complexity of currently available LINACs suitable for LINAC 110. The LINAC 111 is used with controller 103 as example of controller 102 and an electronic portal imaging device (EPID) 155 as an example CT system 150. The EPID 155 includes a low-dose KeV source 156 of KeV photons. Thus the KeV source is an X-ray source. The EPID also includes a sensor array as detector 158.

A LINAC emits electrons, accelerates them as an electron beam in an electric field to high energy and then, using electric or magnetic fields, directs the electron beam onto an object made up of material that tends to absorb the electrons. At the object the electrons are decelerated, giving off the lost kinetic energy as photons with photon energies related to the energy of the electron beam. The resulting X-ray beam is made up of a spectrum of photon energies. The maximum energy is approximately equal to the beam's maximum electric potential times the electron charge. An electron beam accelerated in a one megavolt (MV, 1 MV=$10^6$ volts) electric potential produces X-ray photons of photon energies no greater than about 1 MeV. The mean photon energy in the X-ray beam is only about one third of the maximum energy. Conventionally, the maximum electric potential used by the linear accelerator to accelerate electrons to produce the X-ray beam is used to name the X-ray beam produced. Thus, the energy of diagnostic and therapeutic X-ray beams comprising a mixture of photon energies, is often expressed in kilovolts (kV) or megavolts (MV) rather than keV or MeV. Beam quality and hardness may be improved by special filters, which improve the homogeneity of the X-ray spectrum.

In the illustrated LINAC 111, a control unit 120 causes a modulator 122 to operate an electron gun 112 to emit electrons at a certain rate in an initial electron beam with an initial energy. The electrons are accelerated between electric plates with phased voltages in accelerating waveguide 114 to the maximum energy, e.g., several MV, as is well known in the art. In the electron beam transport component 116, the electron beam is directed onto an object 130 that decelerates and absorbs the electrons. The electron gun 112, accelerating waveguide 114 and electron beam transport component 116 are all maintained in a vacuum by vacuum system 118 to avoid collisions of gas molecules with the electrons in the electron beam, as is well known in the art.

The components of a LINAC include a power supply that provides DC power to modulator 122. The modulator 122 has a pulse forming network which provides direct current (DC) pulses to a thyratron that uses these pulses as a switch to deliver the pulses to the electron gun (112) and simultaneously to a microwave source 124 (e.g., a magnetron or klystron). The electron gun 112 produces a stream of electrons that enter the proximal part of the wave guide 114. The microwave source 124 produces pulsed microwaves which are introduced into the wave guide by a rectangular tube which is filled with high pressure sulfur hexafluoride (SF6)

gas, from gas pressure system 126. The SF6 gas is used because it is stable and won't arc at the high voltages involved. The wave guide 114 is a copper tube with the interior divided by copper discs or diaphragms, and is evacuated to a high vacuum by an ion pump vacuum system 118. The electrons ejected from the electron gun 112 interact with the tuned microwave produced by the microwave source 124, absorb energy, and are accelerated (similar to a surfer riding a wave). A water cooling system 128 keeps the temperature of the waveguide 112 constant.

The components 112, 114, 116, 118, 120, 122, 124, 126 and 128 are well known in the art. See, for example, Karzmark, C. J. *A Primer On Theory And Operation Of Linear Accelerators In Radiation Therapy*, Atlantic Books, ISBN 0944838669, 1997 (hereinafter Karzmark), the contents of which are hereby incorporated by reference as if fully set forth herein, except for terminology that is inconsistent with the terminology used herein.

Once the X-rays are produced at the object 130, the X-ray photons fan out in the forward direction (down in FIG. 1B) and are shaped by several X-ray absorbing or diffracting components (called X-ray optics herein). The fan is shaped into an initial X-ray beam using primary collimators 132. Strong intensity variations across the beam cross section at some X-ray energies are homogenized using a flattening filter 134. The X-ray beam cross section is detected in dual ion chamber 136. The X-ray beam is further shaped by passing through variable channel widths in upper jaws 138 with channel 139 for one horizontal direction and through variable channel widths in lower jaws 140 with channel 141 for the perpendicular horizontal direction. Time variable shaping of beam width during operation according to a treatment plan is provided by the multileaf collimator 142 that includes thin independently moving leaves of tungsten that shape the treatment field. The components 132, 134, 136, 138, 140 and 142 are well known in the art. See, for example, *Karzmark*.

The LINAC 111 is capable of producing X-ray beams with a wide range of energies, e.g., 1 to 25 MV X-ray beams. Such state of the art clinical linear accelerators were designed to be capable of treating: 1) irregularly shaped targets that deform unpredictably during respiratory or gastrointestinal motion, 2) targets of significantly different sizes, 3) lesions of various depths within the body. These capabilities are not necessary for treatment of dysfunctional sympathetic nerves, because these nerves are for the most part superficial, the target is uniform in shape and size, and not dramatically deformed by breathing or gastrointestinal motion.

In some embodiments, a modified device is designed for the precise delivery of high dose, lower photon energy focused beams of radiation to small discrete targets of consistent depth, such as the sympathetic nerves. The device consists of a simplified linear accelerator producing a fixed energy beam selected in a range from about 2 MV to about 6 MV. The reduced maximum energy reduces the amount of shielding that must be provided. Thus, in some embodiments, an apparatus includes an X-ray source that produces an X-ray beam that includes photons with photon energy above 1 million electron and does not include photons with photon energy above six million electron volts.

Figure 2:
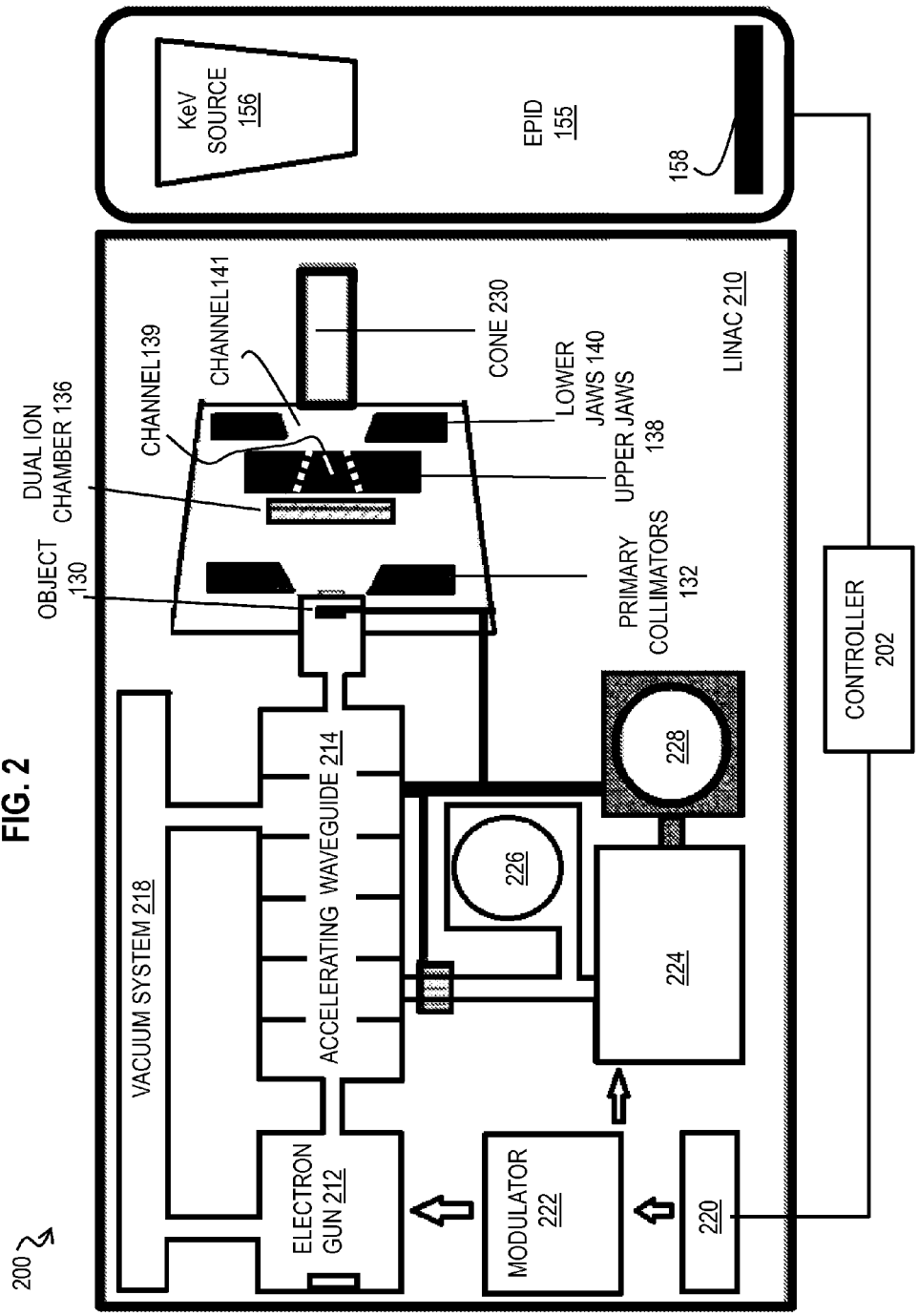
FIG. 2 is a block diagram that illustrates an example modified linear accelerator, according to another embodiment.

FIG. 2 is a block diagram that illustrates an example modified linear accelerator 210, according to another embodiment. The electron gun 212, accelerating waveguide 214, control unit 220, modulator 222, microwave power source 224, gas pressure system 226 and water cooling system 228 are more simply configured to produce a fixed electron beam energy in the range from about 2 MV to about 6 MV. Higher photon energies are not required for the shallow targets presented by sympathetic nerves. Size and weight and complexity of LINAC 210 are reduced by omitting the electron beam transport component 116 and its associated magnets. For example, the bending magnet that is responsible to turn the horizontal beam vertically towards the patient is removed and the beam is directed horizontally towards the patient. This allows a more compact design of the LINAC. The vacuum system 218 is reduced by not having to evacuate the electron beam transport component 116. The object 130 is as described above for LINAC 111. Some conventional LINACs include electron scattering foil that is employed if the object 130 is displaced and treatment is performed with all or part of the electron beam. However, in some embodiments, the electron beam is not used for treatment of the sympathetic nerve targets; and, the electron scattering foil is removed.

The X-ray optics are also reduced and simplified. The X-ray optics include the primary collimators 132, the dual ion chamber 136, upper jaws 138 with channel 139 and lower jaws 140 with channel 141 as described above. However, a flattening filter 134 is omitted because the lower energy X-ray beam is satisfactorily uniform across the beam cross section for the regular shaped targets presented by sympathetic nerves. Given the small diameter of treatment fields for sympathetic nerves, and the capacity to account for residual non-flat dose distributions in the treatment software, no flattening filter is included. Omitting the flattening filter allows for higher dose rates which results in faster dose delivery. Current LINACs allow dose rates up to 2400 monitor units (MU) per minute (min), corresponding to about 24 Gy/min under some conditions.

Similarly, given the small size of sympathetic nerve targets, no field shaping via costly multileaf collimators is necessary. Thus, the multileaf collimator 142 is omitted and replaced by a cone 230 that shapes the beam cross section for one or more of the limited number of targets. This change reduces radiation exposure to the patient from leakage through and between the leaves, and reduces the programming/controls/motors necessary to run the collimators, thus reducing the size, weight and cost of the LINAC 210.

In some embodiments, differently sized cones are switched manually. For example, in some embodiments, one cone 230 is used for targeting the renal sympathetic nerves of all adult patients. A second cone replaces cone 230 for another set of one or more regular shaped targets, such as the thoracic sympathetic nerve targeted to control arrhythmia. Thus, the high energy radiation beam is shaped by interchangeable cones of fixed apertures instead of multileaf collimators. In some embodiments, an adjustable cone/collimator allows automatic adjustment of the field size. Such cones with variable aperture exist and incorporate twelve 60 millimeter tall prism-shaped tungsten-copper alloy segments in two banks of six for shaping the radiation beam. The banks rotate with respect to each other and thus create field variable sizes. See, for example, Echner G G, Kilby W, Lee M, Earnst E, Sayeh S, Schlaefer A, Rhein B, Dooley J R, Lang C, Blanck O, Lessard E, Maurer C R Jr, Schlegel W., "The design, physical properties and clinical utility of an iris collimator for robotic radiosurgery," *Phys Med Biol.*, 54(18):5359-80, 2009 Sep. 21, the entire contents of which are hereby incorporated by reference as if fully set forth herein, except for terminology that is inconsistent with the terminology used herein. Thus, in some of these embodiments, the X-ray source 210 excludes a multi-leaf collimator and further comprises at least one shaping cone 230 configured to target at least one sympathetic nerve in a living body.

The controller 202, used as controller 102, is also simplified and is configured to drive the LINAC for a smaller variety of targets in a subject; in some embodiments. The EPID 155 with source 156 and detector 158 is as described above.

With such a lower energy source, less shielding is needed, and the shield can be mounted on the same support as the LINAC. Thus, in these embodiments, an apparatus includes the lower energy X-ray source, a mounting structure, and a shield mounted on the mounting structure in opposition to the X-ray source to block the X-ray beam from the X-ray source for photons with photon energies not greater than about six million electron volts.

In some embodiments, the modified linear accelerator 210 is mounted on a swing gantry. Also mounted on the same or independent gantry, is a keV source/detector set, such as EPID 155, capable of cone beam CT for 3D anatomy match, portal imaging, and fluoroscopy. In some embodiments, the subject support table 170 is replaced by a dynamic support structure, capable of six direction movement, (positive and negative in each of two horizontal and one vertical dimension). In some embodiments, the support table is capable of pitch and yaw movement, which permits execution of non-coplanar treatment plans and optimization of patient position.

Figure 3A:
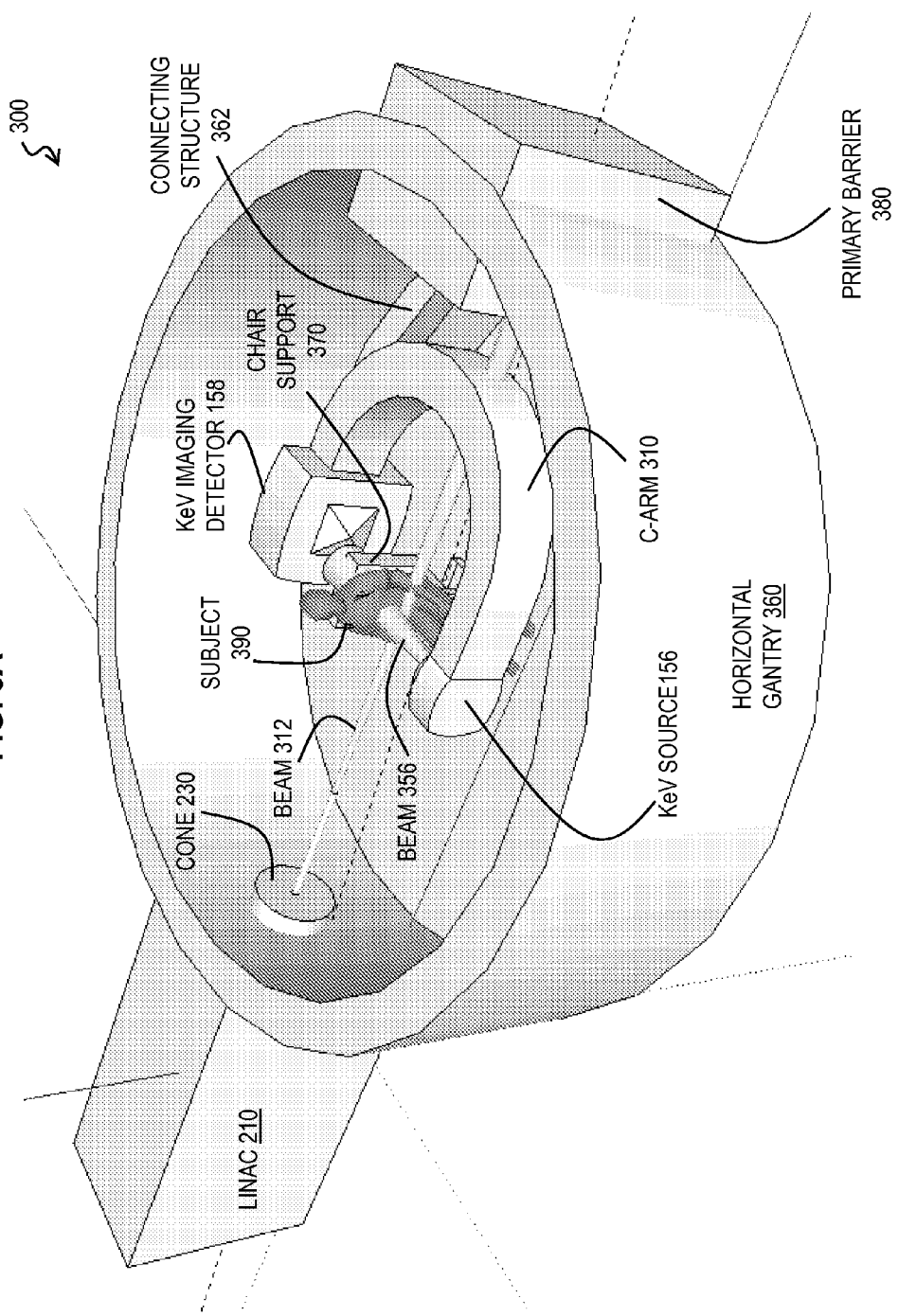
FIGS. 3A to 3C are diagrams that illustrate views of a different example system for radioablation of a sympathetic nerve, according to one embodiment.
Figure 3B:
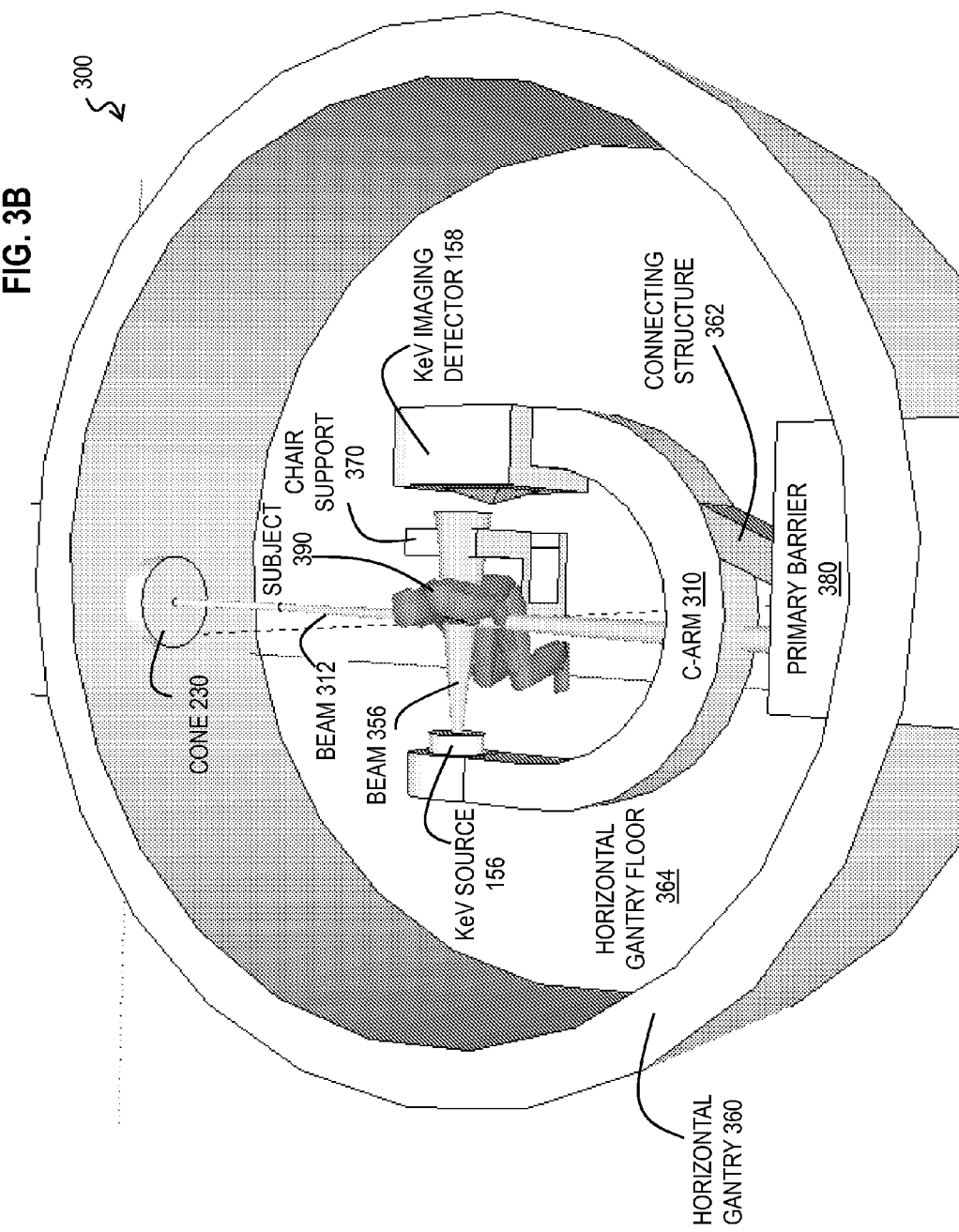
Figure 3C:
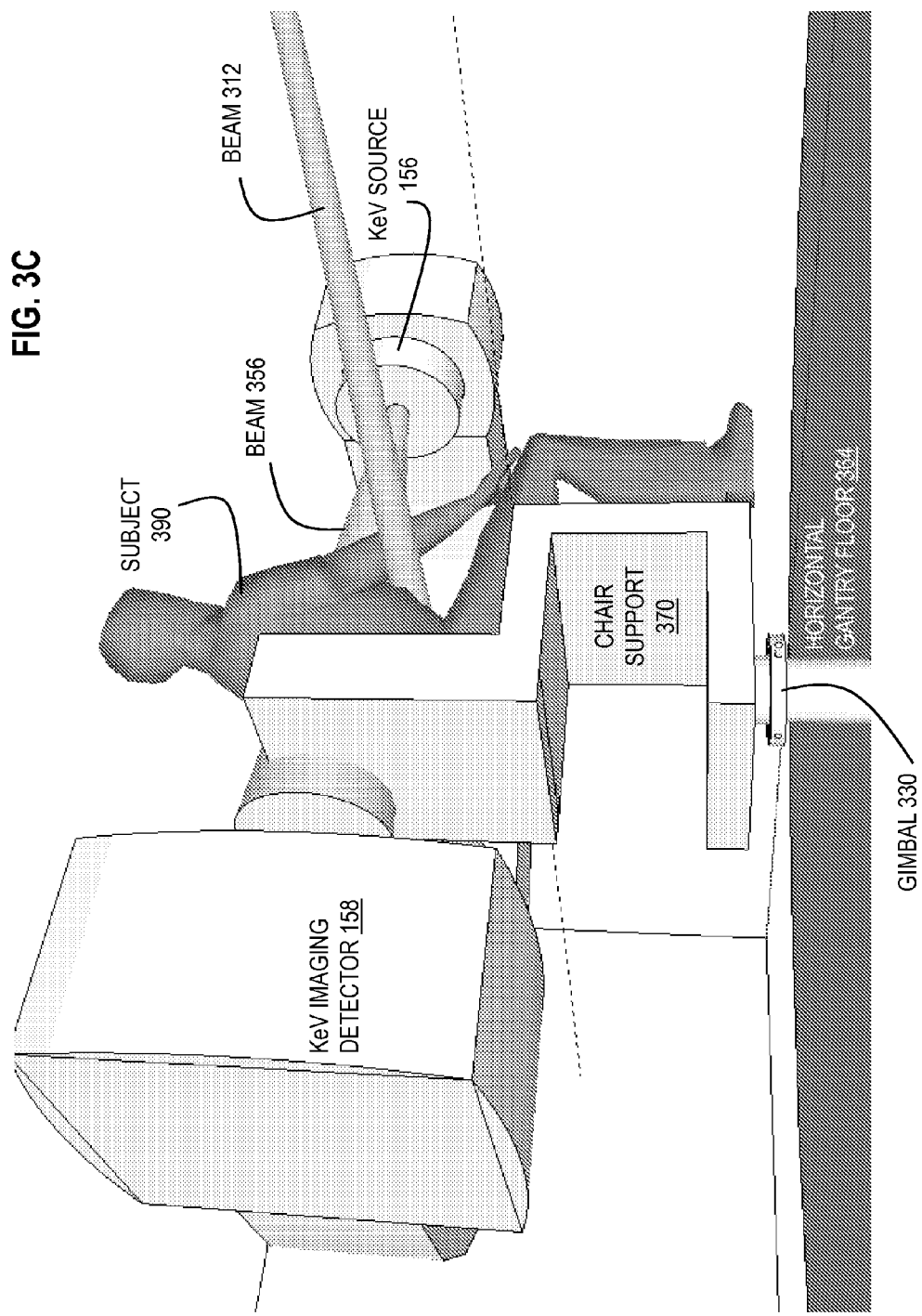

In some embodiments, the modified LINAC 210 is mounted on a horizontal gantry. FIGS. 3A to 3C are diagrams that illustrate views of a different example system 300 for radioablation of a sympathetic nerve, according to one embodiment. FIG. 3A depicts a first perspective view of system 300 from above. In this embodiment, the LINAC 210 is mounted on a horizontal gantry 360 with cone 230 protruding inside. Opposite the LINAC is a primary barrier 380 that acts as a shield to block the highest energy X-rays photons output by the LINAC 210. Because the maximum energy X-ray beam is limited, e.g., to 6 MV, the size of the barrier 380 is limited, thus reducing the total size and weight of horizontal gantry 360. In some embodiments, the other walls of the horizontal gantry also provide some shielding. Again, because the maximum energy X-ray beam is limited, e.g., to 6 MV, the weight of horizontal gantry 360 is limited. An X-ray beam 312 emitted by the LINAC 210 passes through the subject 390, who is seated, as described below, and the X-ray beam 312 is blocked by the primary barrier 380. Thus the apparatus includes a mounting structure (e.g., gantry 360), and the X-ray source 210 and a shield (primary barrier 380) mounted to the mounting structure. The X-ray source produces an X-ray beam that includes photons with photon energy above 1 million electron volts and does not include photons with photon energy above six million electron volts. The shield is mounted to block the X-ray beam from the X-ray source for photons with photon energies not greater than about six million electron volts.

In the line of the beam 312 is a chair support 370 for supporting a subject 390 in a seated position. An advantage of a seated position is to accommodate patients with existing cardiovascular or pulmonary symptoms, who cannot lie flat for long periods of time. In some embodiments, there are arm supports for arms up position or arms down position. In some embodiments, custom made molds fit patients precisely and consistently and are laid over the chair support 370. In some embodiments, the treatment chair has six degrees of freedom for reproducibility of anatomy matching prior to delivery of dose. For patients with cardiovascular disease, for whom lying flat is a challenge, this will be especially helpful. Present treatment beds offer adjustments in height, rotation, and shifts along the superior-inferior axis, and left-right. Newer beds also offer roll and pitch. Thus the chair support 370 in some embodiments is configured to offer six degrees of freedom of adjustment for precise positioning.

The chair is rotatably connected to the horizontal gantry and components fixed thereto. In some embodiments, the horizontal gantry and components fixed thereto are stationary and the chair rotates with the subject. In some of these embodiments, the shielding of the horizontal gantry is provided by burying the system 300 in a floor of a basement. In some embodiments, for the comfort of the patient, the chair and subject do not rotate rapidly, or the gantry 360 and components fixed thereto rotate in the horizontal plane, or some combination. This is possible because of the lower maximum energy of the X-ray beam 312 and corresponding lower weight of the primary barrier 380. Thus, this apparatus includes a subject support, wherein the subject support is disposed between the X-ray source and the shield in rotatable orientation relative to the mounting structure. In the illustrated embodiment, the subject support is a chair that supports a subject in a seated position.

In a pre-determined position relative to the LINAC 210 is a KeV imaging system. For example, a connecting structure 362 fixes the gantry 360 to a C-arm 310 which terminates on the KeV source 156 and KeV imaging detector 158 of a volume imaging system. The KeV source 156 emits a cone beam 356 that passes through the subject 390 in the chair support 370 and impinges on the KeV imaging detector 158. Thus, the apparatus includes a volume imaging system (KeV imaging system 150 or 155) mounted on the mounting structure in a predetermined relationship to the X-ray source. In the illustrated embodiment, the volume imaging system further comprises a different X-ray source (e.g., KeV source 152 or 156) that produces an X-ray frequency with photon energy below about one hundred thousand electron volts.

FIG. 3B depicts a second perspective view of system 300 from above. The LINAC cone 230, horizontal gantry 360, primary barrier 380, connecting structure 362, C-arm 310, KeV source 156, KeV imaging detector 158, chair support 370, seated subject 390, beam 312 and beam 356 are as described above. Also evident is the horizontal gantry floor 364, which is fixed in some embodiments, and rotating with gantry 360 is some embodiments. FIG. 3C depicts a third perspective view of a portion of system 300 from below. The KeV source 156, KeV imaging detector 158, chair support 370, seated subject 390, horizontal gantry floor 364 beam 312 and beam 356 are as described above. FIG. 3C also shows a gimbal 330 that rotatable connects the chair support 370 to the horizontal gantry floor 364.

Although a particular set of components and structures are shown in FIGS. 1A through 3B for purposes of illustration, in various other embodiments more or fewer components and structures providing similar or analogous functions are involved.

The system 100, with LINAC 111 used as LINAC 110, can be operated to ablate an arbitrary target, using the steps of the method depicted in FIG. 4A, described next. In some embodiments, the system 100, with LINAC 111 or LINAC 210 used as LINAC 110, is operated to ablate a sympathetic nerve target, using the steps of the modified method depicted in FIG. 5, as described in more detail below. If LINAC 210 is used, the shielding 180 of system 100 can be reduced. For example, panels 184 and 186 can be omitted. In some embodiments, the system 300, with LINAC 210, is operated to ablate a sympathetic nerve target, using the steps of the method depicted in FIG. 6, described in more detail below.

Figure 6:
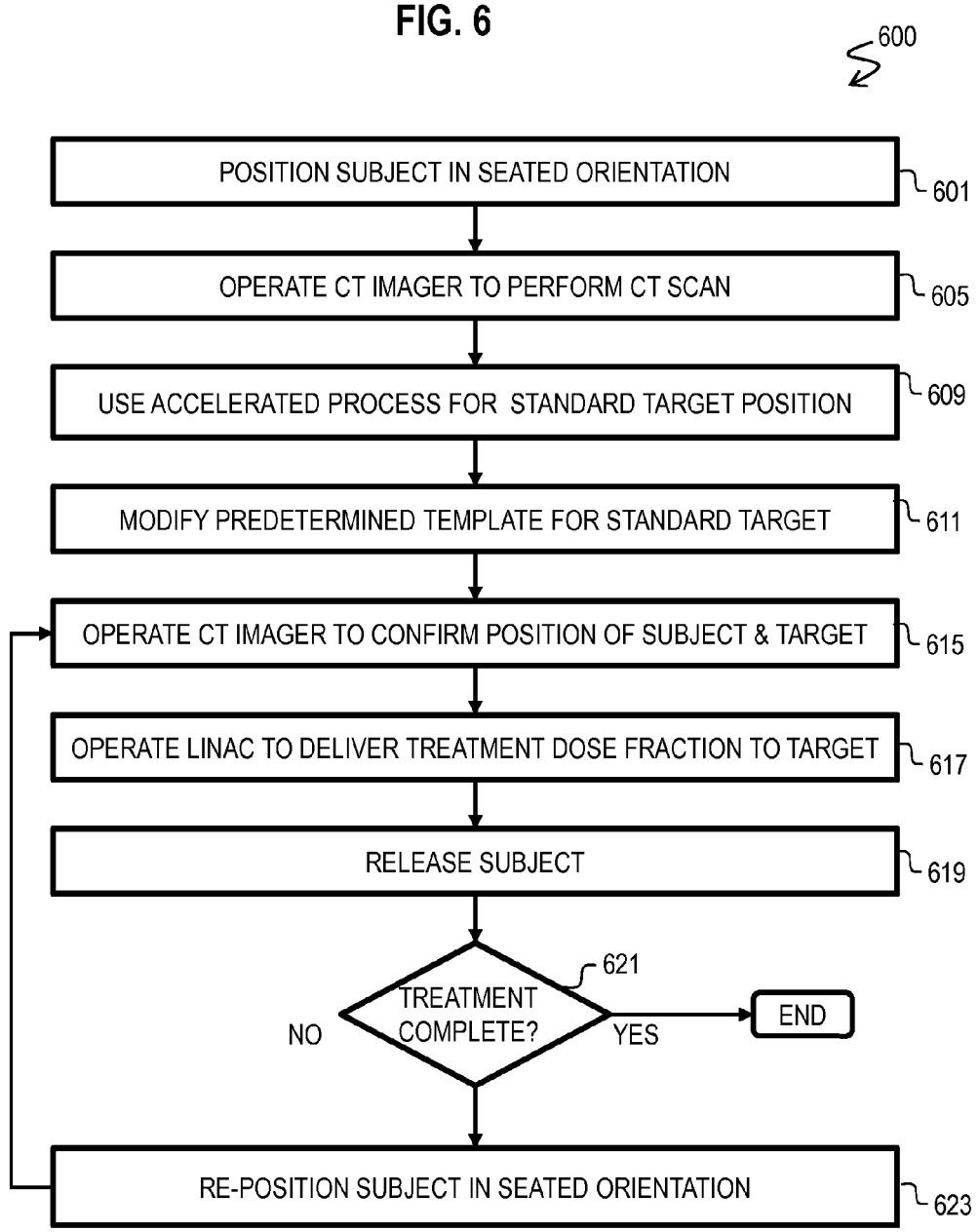
FIG. 6 is a flowchart that illustrates an example process for radioablation of a sympathetic nerve using the system of FIG. 3A, according to one embodiment.

FIG. 4A is a flowchart that illustrates an example process 400 for radioablation of a arbitrary target using the system of FIG. 1A, according to one embodiment. Although steps in FIG. 4A and subsequent flow charts in FIG. 5 and FIG. 6 are shown in a particular order for purposes of illustration, in other embodiments, one or more steps may be performed in a different order or overlapping in time, in series or in parallel, or one or more steps may be omitted or other steps added, or the method is changed in some combination of ways.

In step 401, a subject is positioned in supine orientation in view of the LINAC and volume imaging system. For example, a patient is brought into the clinical CT scanner, placed supine in treatment position (arms on chest, spine aligned for renal sympathectomy, arms above head for thoracic sympathectomy) on translating support 172 and moved so that the target is in view of the CT scanner; and a CT reference point is set. In some embodiments, the patient is also in view of the source of ionizing radiation, such as LINAC 110. Thus, step 401 includes positioning a subject on a support in view of a volume imaging system and an ionizing radiation source.

In step 403, reference points indicated by the device, such as laser beam emitted by the volume imaging system, are tattooed on the subject. For example, three reference laser beams from the device indicate points on the patient's torso that are marked and tattooed on the patient's skin. This is so the patient can leave the area while a treatment solution is obtained and then be re-positioned on the translating support for delivery of the dose of ionizing radiation.

In step 405, the volume imaging system, such as the EPID CT imager 155, is operated to perform a respiration gated CT scan. The CT images are acquired and indexed to phase of the subject's breathing cycle to measure the displacement of the target in successive images. Accounting for such displacement enhances the resolution of determining the target location, size and shape. For example, the patient is scanned through the area to the treated. (For renal sympathetic denervation this would be the kidneys. For thoracic sympathectomy, this would be the thorax.) A respiratory gated scan may be obtained to follow organ motion during the respiratory cycle. The controller 102 controls the operation of the volume imaging system, 150 or 155, and collects and stores the measured and derived images. Thus, this step includes collecting volume image data for the subject based on the volume imaging system.

In step 407 the subject is released to leave the area. For example the subject sits up or relocates to a room or residence to return hours or days later when a treatment solution is available.

In step 409, the scans from the volume imager are analyzed to determine the target location, size and shape and respiration-related target motion. In some embodiments, the determination is based, at least in part, on human input. For example, the patient's CT images are compiled, the respiratory cycle with the least organ motion is identified. The target is identified by a human analyst (renal artery for renal sympathetic denervation, and the thoracic sympathetic ganglion for thoracic sympathectomy). Normal critical structures are contoured by the human analyst to help calculate dose to normal structures. A prescription of dose to the target is given by the human analyst. Acceptable tolerance doses for surrounding critical structures are given by the human analyst. The human analyst indicates whether the treatment plan is to be confined to one plane (coplanar) or not (non-coplanar). The human analyst also determines and indicates whether the dose is delivered in one or more dose fractions. This input is received at the controller 102.

Thus step 409 includes determining location of a treatment portion of a sympathetic nerve in the subject based at least in part on the volume image data. For example, a five centimeter long cylinder with diameter 1 millimeter aligned with the axis of the renal sympathetic nerve is taken as the target size and shape and location to ablate the renal sympathetic nerve. In other embodiments longer and shorter cylinders (such as cylinders about 0.5 centimeters to about 10 centimeters) are used as the target for the treatment portion of the renal sympathetic nerve. In some embodiments, the target is multiple cylinders of similar shape. In some embodiments the target volume is chosen to avoid dangerous doses to surrounding radiosensitive organs, for example the spinal cord; or nearby bowel, urethra and kidney during renal sympathectomy. For example, in some embodiments, the target is chosen at a treatment portion of the renal sympathetic nerve located about midway between the renal pelvis and the takeoff of the renal artery from the aorta. Thus, in some embodiments, step 409 includes determining a treatment portion of the renal sympathetic nerve is about 0.5 to about 10.0 centimeters long.

In some embodiments in which the target is a renal sympathetic nerve, 120 Gy is determined to be an effective dose. It is expected that half this dose is also effective, as is a greater dose. See, for example, *Neurosurg Focus,* 23(6):E3, 2007, showing that a dose of 60 Gy can partially block the trigeminal nerve. Reportedly, atrial fibrillation can be isolated with doses in the 20-30 Gy range. Thus in some embodiments in which the target is a thoracic sympathetic nerve, 20-30 Gy is an effective dose. Thus, in some embodiments even lower doses may be effective, e.g., down to about 10 Gy. Thus in some embodiments, the therapeutic radiation dose is in a range from about 10 Gy to about 180 Gy.

In step 411, the treatment is planned for an arbitrary shaped target. For example, treatment planning software is used to develop a treatment plan that achieves the dose to the target, but stays below the tolerance dose to the surrounding structures. The treatment planning software is executed on one or more computers or chip sets included in controller 102. Such planning software is well known in the art. See for example Eclipse from VARIAN MEDICAL SYSTEMS™ of Palo Alto, Calif., or Ann Van Escha, Laura Tillikainen, Jukka Pyykkonen, Mikko Tenhunen, Hannu Helminen, Sami Siljamaki, Jyrki Alakuijala, Marta Paiusco, Mauro Iori, and Dominique P. Huyskens, "Testing of the analytical anisotropic algorithm for photon dose calculation" *Medical Physics,* 33 (11), 4130-4148, 17 Oct. 2006, the entire contents of which are hereby incorporated by reference as if fully set forth herein, except so far as the terminology is inconsistent with the terminology used herein.

In some embodiments, these algorithms determine an initial plan for operating the system 100, calculate the dose delivered based on properties of the system and a model of the properties of the subject, compares the calculated dose to the desired treatment, determines any differences, and determines changes to the plan to increase the dose on the target or decrease the dose on normal tissue to reduce those differences. Then the steps are repeated with the changed plan until the differences from the desired treatment are within acceptable tolerances. If an acceptable treatment is not determined, the analyst is informed and a different set of desired treatment parameters are determined by the analyst.

Thus step 411 includes determining movement of the ionizing radiation source to apply a therapeutic radiation dose to the treatment portion of the sympathetic nerve based at least in part on the location of the treatment portion of the sympathetic nerve and relative location of the ionizing radiation source to the volume imaging system.

Steps 409 and 411 may take several hours or days, depending on the availability of the analyst.

In step 413, the subject is re-positioned in supine orientation based on the tattoos and reference points. For example, the patient returns for delivery of treatment; and is set up in the same position as for the initial scan. This is confirmed by alignment of CT reference points. For example, the patient is moved until the laser spots from the device align with the tattoos on the skin of the patient.

In step 415, the volume imaging system is operated to confirm the position of the subject and target. For example, three dimensional (3D) anatomy matching by cone-beam CT (CBCT) is performed with the patient on the treatment table, in the treatment position to determine if the currently produced image sufficiently matches the stored images taken during step 405. Such 3D anatomy matching is well known in the art. See, for example, Z. Wang, J Nelson, S Yoo, J Wu, J Kirkpatrick, L Marks and F F Yin, "Refinement of Treatment Setup and Target Localization Accuracy Using Three-Dimensional Cone-Beam Computed Tomography for Stereotactic Body Radiotherapy," *International Journal of Radiation Oncology Bioloy Physics,* 73 (2), 571-577, 1 Feb. 2009; and, F F Yin, Z Wang, S Yoo, J Wu, J Kirkpatrick, N Lanier, J Meyer, C G Willett, L Marks, "Integration of cone-beam CT in stereotactic body radiation therapy" *Technol Cancer Res Treat.* 7(2):133-9, April 2008; and "3D matching for setup of pediatric patients," *J Appl Clin Med Phys.* 11(4), 3388, 11 Oct. 2010; and, "3D matching for mobile abdominal targets," *J Med Case Reports.,* 4, 329, 19 Oct. 2010; and, "3D matching with 1 mm accuracy," *Int J Radiat Oncol Biol Phys.,* 8 Sep. 2010; and, "Automated 3D matching," *Med Phys.,* 37(7), 3677-86, July 2010, the contents of each of which are hereby incorporated by reference as if fully set forth herein, except for terminology that is inconsistent with the terminology used herein. Thus step 415 also includes determining location of a treatment portion of a sympathetic nerve in the subject based at least in part on the volume image data. In some embodiments, the target is a portion of a renal sympathetic nerve. In some embodiments, the target is a portion of a thoracic sympathetic nerve.

In step 417, the LINAC 110 is operated according to the treatment plan to deliver the treatment dose fraction to the target. The controller 102 operates the LINAC 102 based on the treatment plan. Treatment dose can be delivered in either 1 fraction, or divided into many fractions. Thus step 417 includes, operating the ionizing radiation source to deliver the therapeutic radiation dose to the treatment portion of the sympathetic nerve.

In step 419, the subject is released. For example, following treatment delivery, the patient is allowed to go home.

In step 421, it is determined whether treatment is complete. If so, the process ends. Otherwise the process passes back to step 413 to re-position the subject on the subject support system. For example, it is determined during step 421 whether the last treatment dose fraction has been delivered. In some embodiments, if the patient is on long term follow up, it is determined whether there is insufficient reduction in blood pressure. If not, the steps described above are repeated, in some embodiments.

Figure 4B:
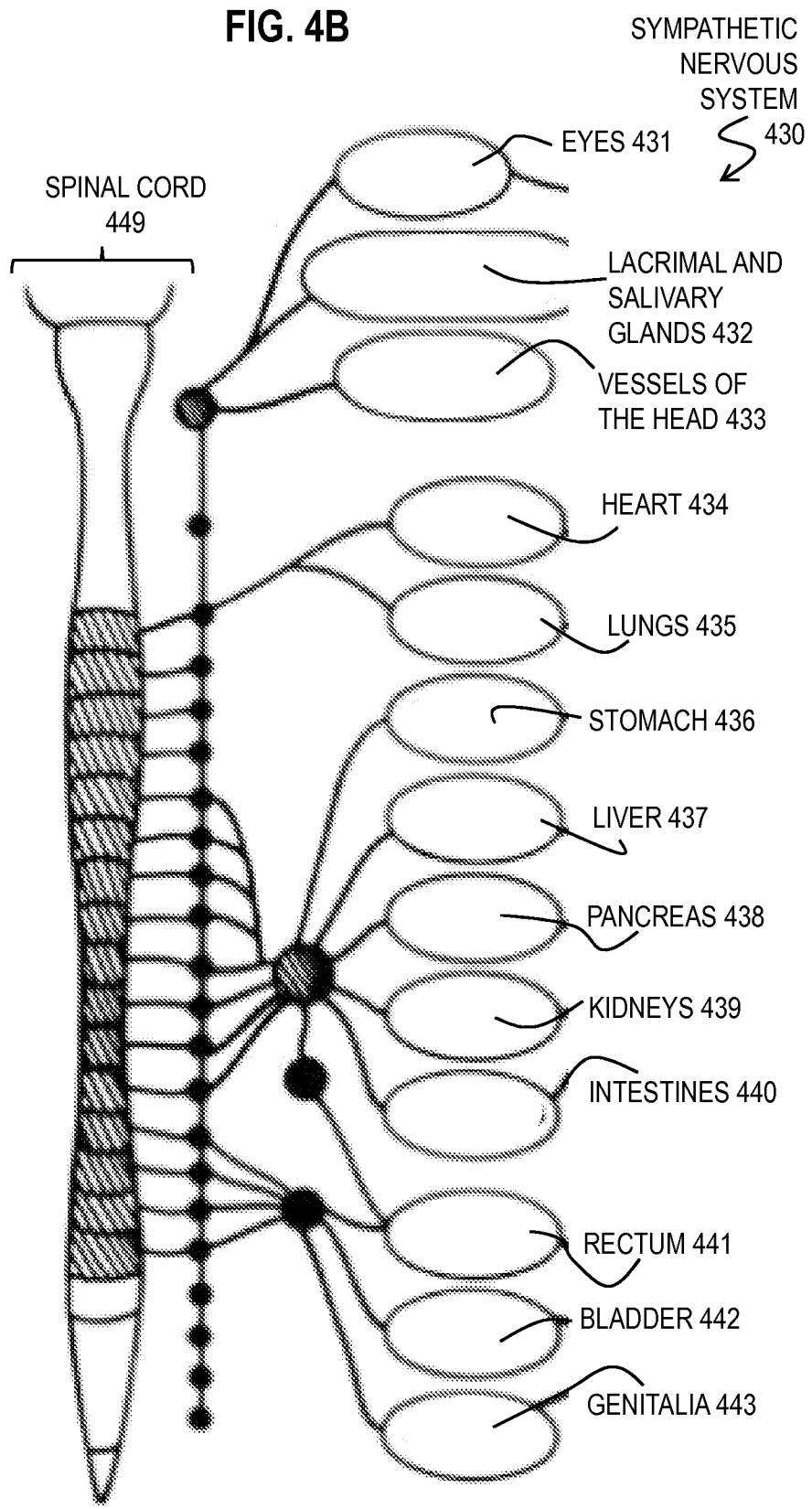
FIG. 4B is a block diagram that illustrates the sympathetic nerve system.
Figure 4C:
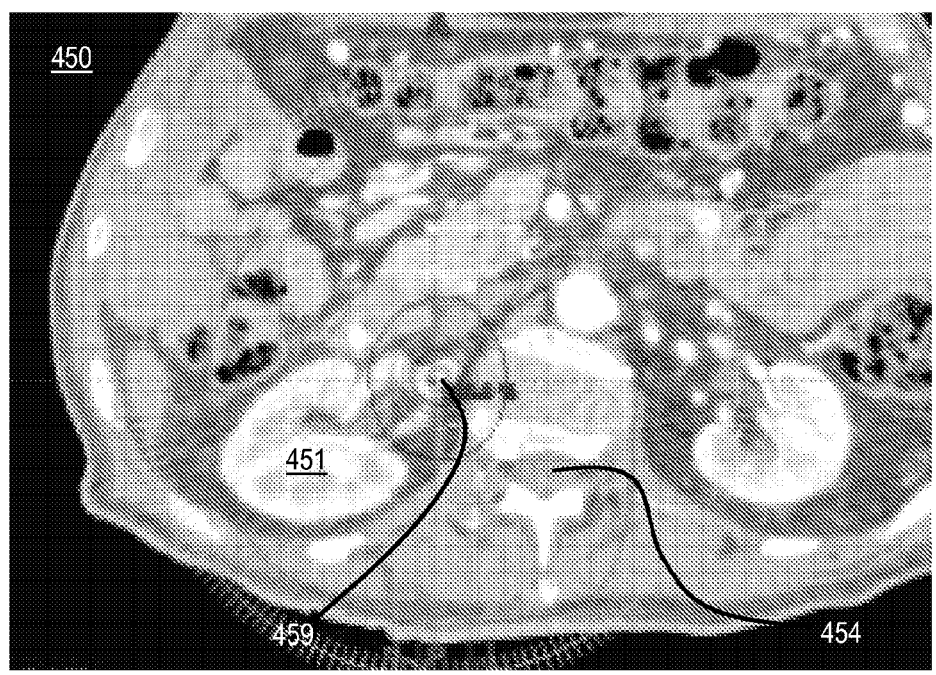
FIG. 4C is an image that illustrates example CT cross section of a human showing a target volume overlapping a treatment portion of a renal sympathetic nerve, according to an embodiment.
Figure 4D:
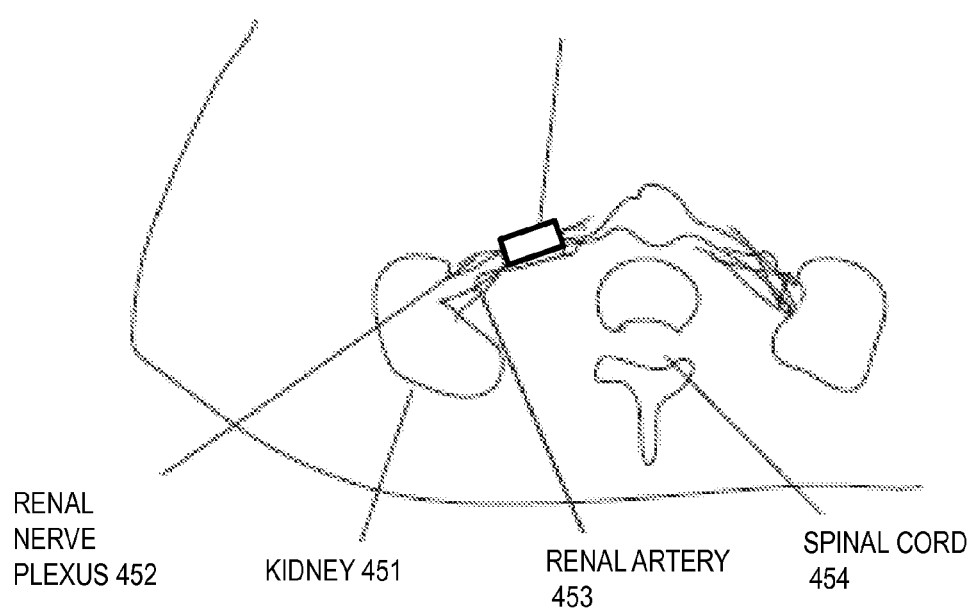
FIG. 4D is a diagram that illustrates items evident in the image of FIG. 4C, according to an embodiment.
Figure 4E:
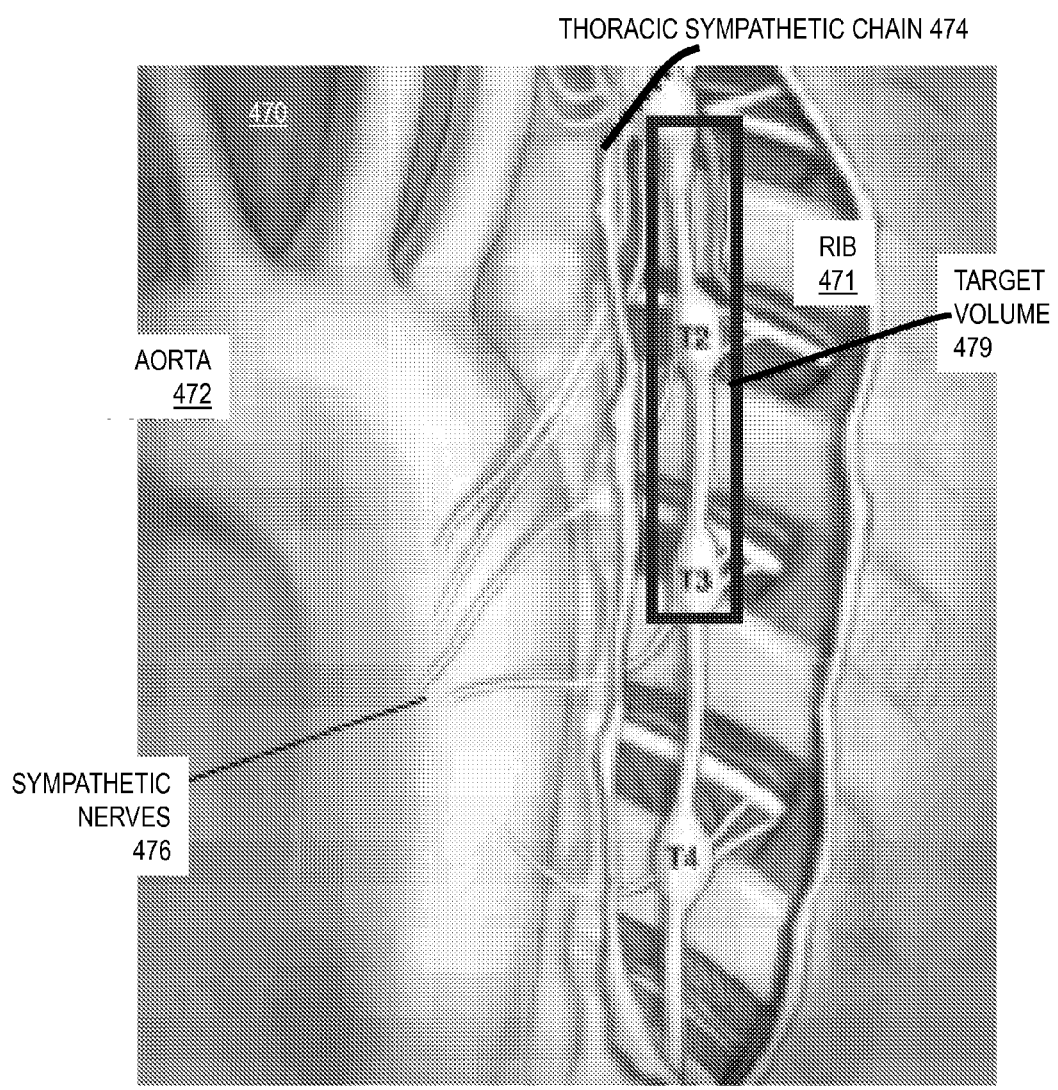
FIG. 4E is a diagram that illustrates a target volume overlapping a treatment portion of a thoracic sympathetic nerve, according to an embodiment.

In some embodiments the process of FIG. 4A is used to target a sympathetic nerve. FIG. 4B is a block diagram that illustrates the sympathetic nervous system 430. The sympathetic nervous system 430 is engaged in a "fight or flight" response of an organism; and runs parallel to the spinal cord 490 to which it is connected at various junctions. The nerves of the sympathetic nervous system connect to various organs represented in the diagram by ovals, including eyes 431, lacrimal and salivary glands 432, vessels of the head 433, heart 434, lungs 435, stomach 436, liver 437, pancreas 438, kidneys 439, intestines 440, rectum 441, bladder 442 and genitalia 443. FIG. 4C is an image 450 that illustrates an example CT cross section of a human showing a target volume 459 overlapping a treatment portion of a renal sympathetic nerve, according to an embodiment. The location of a kidney 451 and spinal cord 454 are indicated. FIG. 4D is a diagram that illustrates items evident in the image of FIG. 4C, according to an embodiment; including the kidney 451, renal nerve plexus 452, renal artery 453, spinal cord 454 and target volume 459. FIG. 4E is a diagram 470 that illustrates a target volume overlapping a treatment portion of a thoracic sympathetic nerve, according to an embodiment. A rib 471, the aorta 472 thoracic sympathetic chain 474 and individual sympathetic nerves 476 re depicted, as is an example target volume 479.

The process of FIG. 4A can be used to target a sympathetic nerve using existing equipment and procedures. However, in some embodiments, some of the steps of process 400 are accelerated or omitted when targeting a portion of a sympathetic nerve, as shown in FIG. 5. FIG. 5 is a flowchart that illustrates an example process 500 for radioablation of a sympathetic nerve using the system 100 of FIG. 1A, according to one embodiment. These efficiencies are achieved by changes in software capability and practice. For example, in the illustrated embodiment depicted in FIG. 5, steps analogous to steps 403 and 413 are omitted, and steps analogous to steps 409 and 411 are accelerated. Because the target, the prescription and the retroperitoneal anatomy are very consistent amongst different patients, a template is used to quickly apply a best fit pre-existing treatment plan to this patient, and then optimized in real time, e.g., using existing treatment solution software.

In step 501, a subject is positioned in supine orientation in view of the LINAC or other source of ionizing radiation and volume imaging system, as described above for step 401; but, no tattooing is necessary because of the accelerated process, and, thus, no step analogous to step 403 is included. In various embodiments, the ionizing radiation beam is derived from a variety of different sources, including S-band, X-band, and UNATRON™ linear accelerators from VARIAN MEDICAL SYSTEMS™ of Palo Alto, Calif., or radioactive sources like Cobalt-60, alone or in any combination.

In step 505, the volume imaging system, such as the EPID CT imager, is operated to perform a respiration gated CT scan, as described above for step 405. For example, the patient is scanned through the kidneys for renal sympathectomy and through the thorax for thoracic sympathectomy. The controller 102 controls the operation of the CT imaging system 150 or 155 and collects, computes and stores the measured and derived images. Because the next steps are essentially automatic, they are performed rapidly; so the subject stays in place and no step analogous to step 407 is included.

In step 509, an accelerated process is used to determine a standard target size, shape, location and respiration-related target motion based, at least in part, on the scans from the volume imager. In some embodiments, the determination is made with little human input. For example, the respiratory cycle with the least target motion is predetermined. Auto-contouring software is used to delineate normal structures. Such auto contouring software is well known in the art. See, for example, MimVista from MIM SOFTWARE INC.™ of Cleveland, Ohio. The target, (e.g., a portion of the renal artery for renal sympathetic denervation, or a portion of the thoracic sympathetic ganglion for thoracic sympathectomy) is identified by the physician by a simple input operation, such as a point and click using a mouse or touch screen on single image showing a cross section of the sympathetic nerve.

Any method may be used to receive predetermined data. For example, in various embodiments, the data is included as a default value in software instructions, is received as manual input from a network administrator on the local or a remote node, is retrieved from a local file or database, or is sent from a different node on a network, either in response to a query or unsolicited, or the data is received using some combination of these methods.

A predefined prescription of dose to the target is provided, which is optionally presented to and adjusted slightly by the human analyst. Predetermined acceptable tolerance doses for surrounding critical structures are provided, which are optionally presented to and adjusted slightly by the human analyst. A predetermined coplanar or non-coplanar treatment option is provided, which is optionally presented to and adjusted by the human analyst. The predetermined plan also indicates whether the dose is delivered in one or more dose fractions, which is optionally presented to and adjusted by the human analyst. These determinations are made at the controller 102.

In step 511, a predetermined treatment plan template is modified slightly. For example, treatment planning software is used with an initial plan for operating the system 100 for a typical renal (or thoracic) sympathetic nerve denervation, e.g., targeting a one centimeter long section of the renal sympathetic nerve adjacent to the kidneys. The treatment planning software is executed until the differences from the desired treatment are within acceptable tolerances, which should take a few iterations that can be executed on the order of about one minute. Thus, unlike steps 409 and 411, steps 509 and 511 are expected to take only a few minutes; and, no step analogous to step 413 is included. Thus, in this embodiment, both collecting the volume image data and operating the ionizing radiation source to deliver the therapeutic radiation dose are performed before removing or re-positioning the subject.

In step 515, the volume imaging system is operated to confirm the position of the subject and target, as described above for step 415. For example, the 3D anatomy matching by cone-beam CT (CBCT) is performed with the patient on the treatment table, in the treatment position to determine if the currently produced image sufficiently matches the stored images taken in step 505. In some embodiments, step 515 is omitted. In some embodiments, step 515 is skipped unless and until step 523 is performed, as described below.

In step 517, as in step 417, the LINAC 110 or other source of ionizing radiation is operated according to the treatment plan to deliver the treatment dose fraction to the target. The controller 102 operates the LINAC 110 or other source of ionizing radiation based on the treatment plan. Treatment dose can be delivered in either 1 fraction, or divided into many fractions.

In step 519, as in step 419, the subject is released. For example, following treatment delivery, the patient is allowed to go home.

In step 521, as in step 421, it is determined whether treatment is complete. If so, the process ends. Otherwise, in step 523, the subject is re-positioned in supine orientation. For example, the patient returns for delivery of treatment; and is set up in same position as initial scan. This is confirmed in step 515, described above.

Due to the unique clinical features of these kinds of treatments, in some embodiments, the modified LINAC 210 that is cheaper to manufacture, install and maintain, is used as LINAC 110 in system 100 with the improved and faster workflow of process 500 depicted in FIG. 5.

FIG. 6 is a flowchart that illustrates an example process 600 for radioablation of a sympathetic nerve using the system 300 of FIG. 3A, according to one embodiment. This system 300 also employs the LINAC 210 that is cheaper to manufacture, install and maintain. Further, system 300 allows a patient to be treated in the seated position that is preferable for some cardiac patients. Process 600 parallels process 500 except for the orientation of the subject.

In step 601, a subject is positioned in seated orientation on chair support 370 in view of the LINAC 210 and volume imaging system 155 of system 300. In some embodiments, step 601 includes forming a patient specific molded cushion and placing that cushion on the chair support 370 before positioning the patient on the cushion and chair support 370.

In step 605, as in step 505, the volume imaging system, such as the EPID CT imager, is operated to perform a respiration gated CT scan, as described above for step 505.

In step 609, as in step 509, an accelerated process is used to determine a standard target size, shape, location and respiration-related target motion based, at least in part, on the scans from the volume imager and statistical or historical or normative conditions. In some embodiments, the determination is made with little human input.

In step 611, as in step 511, a predetermined treatment plan template is modified slightly. For example, treatment planning software is used with an initial plan for operating the system 300 for a typical renal (or thoracic) sympathetic nerve denervation, e.g., targeting a one centimeter long section of the renal sympathetic nerve adjacent to the kidneys. The treatment planning software is executed until the differences from the desired treatment are within acceptable tolerances, which should take a few iterations that can be executed on the order of about one minute. Thus, unlike steps 409 and 411, steps 609 and 611 are expected to take only a few minutes.; and, no step analogous to step 413 is included.

In step 615, as in step 515, the volume imaging system is operated to confirm the position of the subject and target. For example, the 3D anatomy matching by cone-beam CT (CBCT) is performed with the patient seated on the chair support 370, in the seated treatment position to determine if the currently produced image sufficiently matches the stored images taken in step 605. In some embodiments, step 615 is omitted. In some embodiments, step 615 is skipped unless and until step 623 is performed, as described below.

In step 617, the LINAC 210 is operated according to the treatment plan to deliver the treatment dose fraction to the target. The controller 202 operates the LINAC 210 based on the treatment plan. Treatment dose can be delivered in either 1 fraction, or divided into many fractions. In these embodiments of the treatment plan, the movement of the LINAC comprises at least a partial synchronized rotation and revolution in a horizontal plane as the gantry 360 revolves in a horizontal plane. If the treatment is non-coplanar, then the movement further comprises at least a partial synchronized rotation and revolution in a plane at a small angle to the horizontal plane or a tilt or translation of the chair support 360. For example, for non-co-planar treatments, in some embodiments the ring housing the primary energy source is configured to pivot. In some embodiments, the chair support immobilizing the patient is configured to pivot at gimbal 330. In some embodiments, the LINAC beam 112 rotates and is displaced in one plane, e.g., the vertical plane. In some embodiments, the translating support 172 or LINAC 110 is translated or tilted with respect to the first plane after one rotation and displacement.

In step 619, as in step 519, the subject is released. For example, following treatment delivery, the patient is allowed to return home.

In step 621, as in step 521, it is determined whether treatment is complete. If so, the process ends. Otherwise, in step 623, the subject is re-positioned in seated orientation on any custom cushion molded for the patient. For example, the patient returns for delivery of treatment; and is set up in the same position as in the initial scan. This is confirmed in step 615, described above.

Applicants have discovered that resistant hypertension (whether refractory to the best achievable oral therapy, due to non-adherence or established disease resistance) can each be treated by selective radioablation of renal sympathetic nerves. This is the case for both hypertension that is otherwise without symptoms, and hypertension in the context of, and contributing to, debilitating conditions like kidney failure and congestive heart disease. In addition to hypertension, certain types of cardiac arrhythmia can also be treated by selective radioablation of the thoracic sympathetic chain including patients with dilated cardiomyopathy related multifocal ventricular tachycardia, Long-QT Syndrome, and catecholaminergic polymorphic ventricular tachycardia (CPVT). The new methods produce local and systemic effects without the systemic side effects of oral medications. High doses of focused radiation can be delivered to sites of sympathetic nerve dysfunction by an external beam method.

Radiotherapy has traditionally been reserved for oncology patients, given the general wariness of radiation oncologists and other medical practitioners towards long term side-effects of radiation exposure, including increased risk of secondary malignancies. Indeed, early in the history of the specialty, radiotherapy was used to treat acne in teenagers, which led to very regrettable long-term carcinogenic effects. Since that time, improvements in technology has permitted the application of large doses of radiation to millimeter volumes with sub-millimeter precision. Despite this advancement, radiotherapy is employed in the benign setting mostly in the context of 1) very small targets, such as the trigeminal nerve for treatment of intractable facial pain, and 2) patients with limited life expectancy, such as hip replacement geriatric patients, for the prevention of heterotrophic ossification. More recently, retrospective studies have demonstrated no increase in secondary cancer risk in patients treated with high dose radiation to a small area, otherwise known as stereotactic radiosurgery (Neurosurg 60:60 (2007))

Figure 7A:
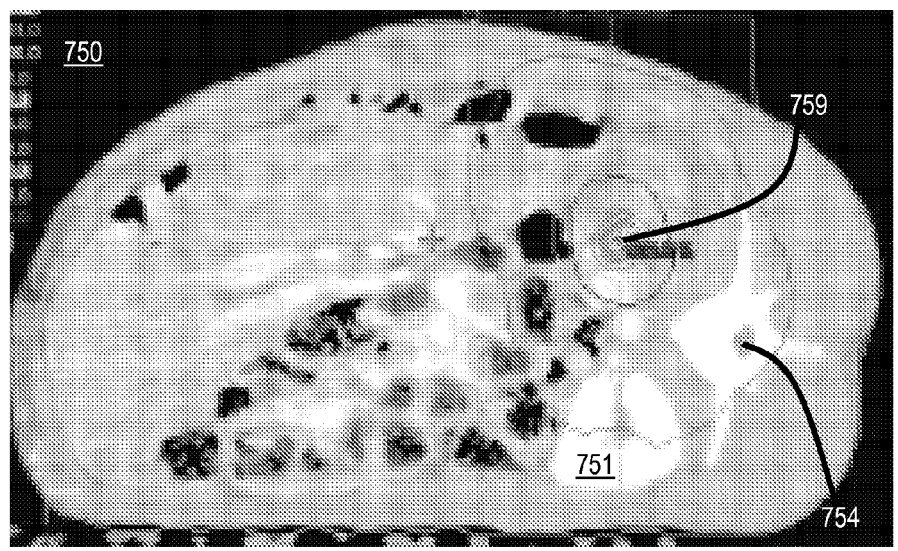
FIG. 7A is an image that illustrates example CT cross section of a minipig showing a target overlapping a treatment portion of a renal sympathetic nerve, according to an embodiment.
Figure 7B:
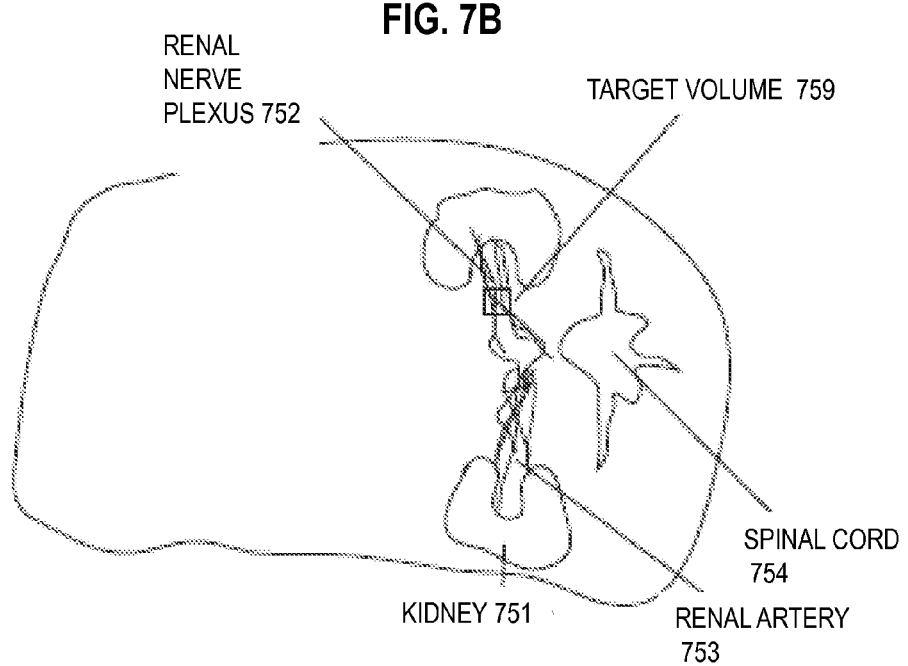
FIG. 7B is a diagram that illustrates items evident in the image of FIG. 7A, according to an embodiment.

The effectiveness of the methods described herein is exemplified in an embodiment in which the subject is a pig and the target is a portion of the renal sympathetic nerve. Minipigs were subjected to surgical renal artery stenosis to induce systemic hypertension and sympathetic overactivity. Blood pressure was measured using cuff manometry and compared to pretreatment baseline. Computed tomography with intravenous contrast was performed to identify the renal artery and vein and surrounding tissue. FIG. 7A is an image 750 that illustrates example CT cross section of a minipig showing a target overlapping a treatment portion of a renal sympathetic nerve, according to an embodiment. A kidney 751, spinal cord 754 and target volume 759 are indicated. FIG. 7B is a diagram that illustrates items evident in the image of FIG. 7A, according to an embodiment; including the kidney 751, renal nerve plexus 752, renal artery 753, spinal cord 754 and target volume 759. A treatment plan was generated targeting the renal nerve plexus surrounding the renal artery. Stereotactic radiotherapy to the target volume was performed with peak dose of 120 Gy. Following treatment, swine underwent cuff manometry to assess blood pressure response to stereotactic treatment to the renal nerve plexus.

FIG. 7C is a graph 700 that illustrates example results of radioablation of a renal sympathetic nerve, according to an embodiment. The horizontal axis 702 indicates elapsed time in days from the event of surgical renal stenosis, indicated by time 712. The vertical axis 704 indicates systolic blood pressure in millimeters of Mercury (mm Hg). The dashed line 706 indicates the boundary between hypertensive (high blood pressure) above the line 706 and normotensive (normal blood pressure) below the line. The trace 720 indicates the measured systolic blood pressure of the subject pig.

As shown by trace 720, after surgical renal stenosis, the blood pressure of the subject rises to a peak value over 160 mm Hg in two weeks (14 days). Then, stereotactic radiotherapy to the renal nerve was performed using the method 400 of FIG. 4A at time 714 (14 days). After the non-invasive radiotherapy, the subject's blood pressure steadily dropped over the next two weeks to return to normal at 28 days, where it remained for the extent of the experiment. This indicates the effectiveness of the methods presented herein.

Existing methods of blood pressure control (for the most part singular or combination oral agents), unfortunately, fail to achieve targets of blood pressure reduction in the majority of treated patients. This can be due to both patient non-adherence to lifelong pharmacotherapy for a silent condition, and genuine disease resistance. In an especially vulnerable patient population, for example dialysis patients, adequate control of blood pressure reduces mortality risk by 50%. Congestive heart failure, a condition affecting 5.3 million people, has a similar development of resistance over time to medication management, due to up-regulation of renal and sympathetic nerve activity. Blood pressure control in this context similarly reduces mortality. Inherited or acquired malignant ventricular arrhythmias are by definition life threatening, and in selected patients, sympathetic nervous system activation leads to life threatening arrhythmias. In these patients, selective thoracic sympathetic nerve radioablation may significantly prolong and improve life.

For this new indication of selective sympathetic nerve radioablation, some embodiments described here have several advantages over existing systems for stereotactic body radiotherapy, including reduced cost, for both initial purchase and maintenance. Existing systems for stereotactic body radiotherapy are designed to utilize a variety of beam energies for lesions of different depths, utilize multileaf collimators for targets of different sizes and irregular shapes, and utilize variable output to shape a uniform dose across an irregularly shaped target. Because the targets of selective sympathetic nerve radioablation, including the renal sympathetic nerve and thoracic sympathetic nerve, are consistent in their size, location, depth, and shape, none of these features are necessary. The LINAC 210 used in some embodiments has fixed energy, fixed but interchangeable aperture, and fixed output. The unnecessary features are stripped to produce a system that is significantly less costly to own and maintain, just as precise, and more reliable.

Some embodiments also offer the advantage of improved safety and reduced shielding requirements. Because existent clinical linear accelerator systems are designed to accommodate targets of variable depths, they utilize a range of energies, typically from 4 MV to 15 MV. As energies increase, the shielding requirements increase. At the higher 15 MV energy range, there is a significant neutron contamination that requires additional precautions. Even if a system is never used at the 15 MV energy, that it is capable of 15 MV output is sufficient to require these additional shielding and precautions. Because both renal sympathetic nerves and thoracic sympathetic nerves are superficial, a maximal energy of 6 MV is sufficient. Thus the shielding requirements for this dedicated device, and cost of installation, are significantly reduced.

Some embodiments also offer the advantage of standardized dosimetry. Existing treatment planning systems are made to accommodate wide ranging requirements of target size, shape, depth, deformation with movement, location, and avoidance structures. Each patient is traditionally planned anew. In the case of selective sympathetic nerve ablation, the target size, shape, depth, and deformation are consistent from patient to patient. Thus an algorithm that presents a preselected plan can be rapidly fine tuned to the individual patient, greatly enhancing both workflow and safety.

Some embodiments also offer the advantage of generalized utilization. In addition to selective sympathetic nerve ablation, the LINAC 210 is capable of executing a variety of treatment plans traditionally reserved for full featured clinical linear accelerators. These indications include but are not limited to nerve ablation for trigeminal neuralgia, arteriovenous malformations, brain lesions (metastatic lesions to the brain, meningiomas, etc), boost for head and neck cancer, acoustic neuromas, chordomas, metastatic lesions to the spine, early primary lung lesions, metastatic lesions to the liver, among others. The 3D anatomy matching and respiratory gating capabilities of this device ensures precise delivery of radiation to a wide range of target sites.

At least some steps of the processes described herein for determining treatment plans and operating ionizing radiation sources may be implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such example hardware for performing the described functions is detailed below.

Figure 8:
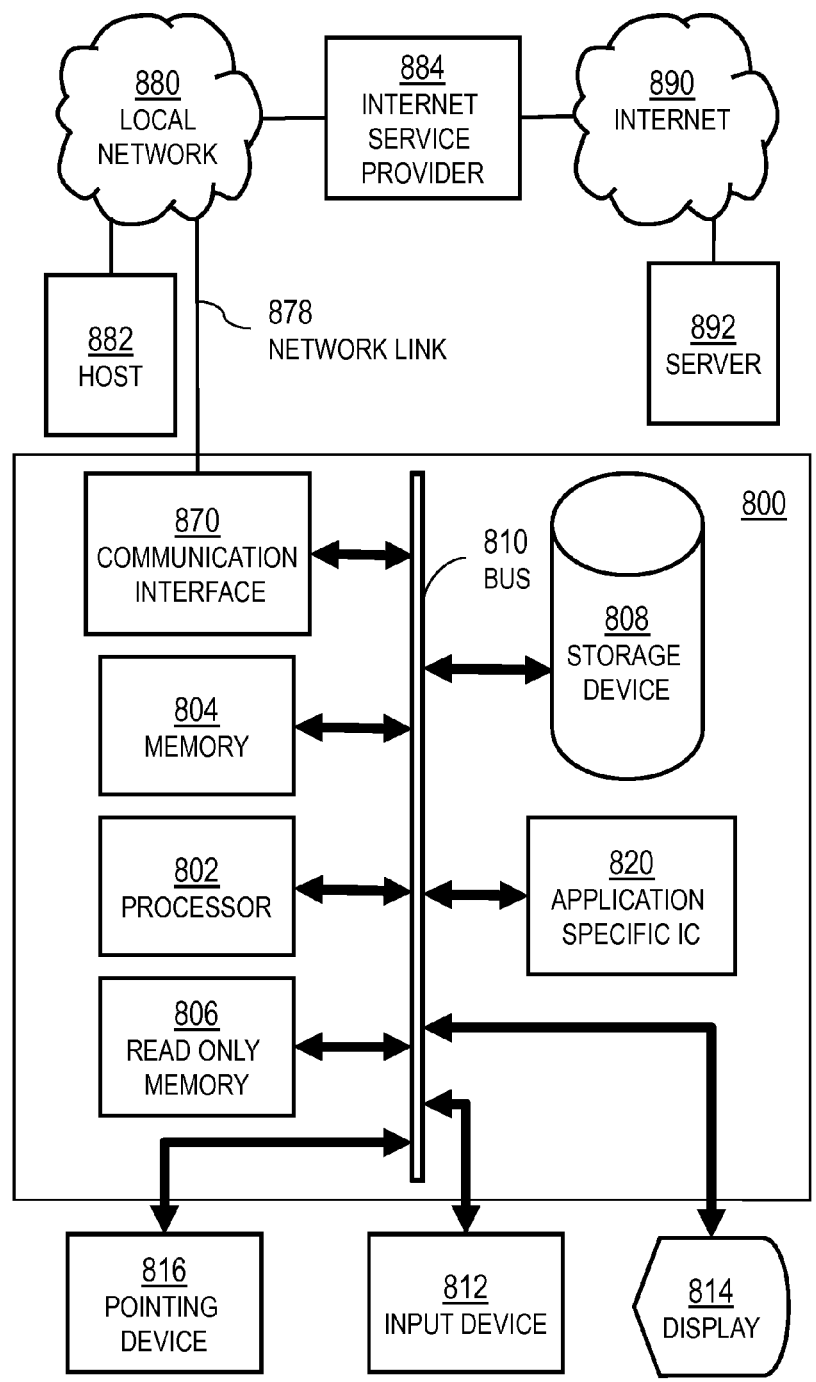
FIG. 8 is a diagram of hardware that can be used to implement an embodiment of the invention.

FIG. 8 illustrates a computer system 800 upon which an embodiment of the invention may be implemented. Computer system 800 includes a communication mechanism such as a bus 810 for passing information between other internal and external components of the computer system 800. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range.

A bus 810 includes one or more parallel conductors of information so that information is transferred quickly among devices coupled to the bus 810. One or more processors 802 for processing information are coupled with the bus 810.

A processor 802 performs a set of operations on information. The set of operations include bringing information in from the bus 810 and placing information on the bus 810. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 802, such as a sequence of operation codes, constitute processor instructions, also called computer system instructions or, simply, computer instructions. Processors may be implemented as mechanical, electrical, magnetic, optical, chemical or quantum components, among others, alone or in combination.

Computer system 800 also includes a memory 804 coupled to bus 810. The memory 804, such as a random access memory (RAM) or other dynamic storage device, stores information including processor instructions. Dynamic memory allows information stored therein to be changed by the computer system 800. RAM allows a unit of information stored at a location called a memory address to be stored and retrieved independently of information at neighboring addresses. The memory 804 is also used by the processor 802 to store temporary values during execution of processor instructions. The computer system 800 also includes a read only memory (ROM) 806 or other static storage device coupled to the bus 810 for storing static information, including instructions, that is not changed by the computer system 800. Some memory is composed of volatile storage that loses the information stored thereon when power is lost. Also coupled to bus 810 is a non-volatile (persistent) storage device 808, such as a magnetic disk, optical disk or flash card, for storing information, including instructions, that persists even when the computer system 800 is turned off or otherwise loses power.

Information, including instructions, is provided to the bus 810 for use by the processor from an external input device 812, such as a keyboard containing alphanumeric keys operated by a human user, or a sensor. A sensor detects conditions in its vicinity and transforms those detections into physical expression compatible with the measurable phenomenon used to represent information in computer system 800. Other external devices coupled to bus 810, used primarily for interacting with humans, include a display device 814, such as a cathode ray tube (CRT) or a liquid crystal display (LCD), or plasma screen or printer for presenting text or images, and a pointing device 816, such as a mouse or a trackball or cursor direction keys, or motion sensor, for controlling a position of a small cursor image presented on the display 814 and issuing commands associated with graphical elements presented on the display 814. In some embodiments, for example, in embodiments in which the computer system 800 performs all functions automatically without human input, one or more of external input device 812, display device 814 and pointing device 816 is omitted.

In the illustrated embodiment, special purpose hardware, such as an application specific integrated circuit (ASIC) 820, is coupled to bus 810. The special purpose hardware is configured to perform operations not performed by processor 802 quickly enough for special purposes. Examples of application specific ICs include graphics accelerator cards for generating images for display 814, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 800 also includes one or more instances of a communications interface 870 coupled to bus 810. Communication interface 870 provides a one-way or two-way communication coupling to a variety of external devices that operate with their own processors, such as printers, scanners and external disks. In general the coupling is with a network link 878 that is connected to a local network 880 to which a variety of external devices with their own processors are connected. For example, communication interface 870 may be a parallel port or a serial port or a universal serial bus (USB) port on a personal computer. In some embodiments, communications interface 870 is an integrated services digital network (ISDN) card or a digital subscriber line (DSL) card or a telephone modem that provides an information communication connection to a corresponding type of telephone line. In some embodiments, a communication interface 870 is a cable modem that converts signals on bus 810 into signals for a communication connection over a coaxial cable or into optical signals for a communication connection over a fiber optic cable. As another example, communications interface 870 may be a local area network (LAN) card to provide a data communication connection to a compatible LAN, such as Ethernet. Wireless links may also be implemented. For wireless links, the communications interface 870 sends or receives or both sends and receives electrical, acoustic or electromagnetic signals, including infrared and optical signals, that carry information streams, such as digital data. For example, in wireless handheld devices, such as mobile telephones like cell phones, the communications interface 870 includes a radio band electromagnetic transmitter and receiver called a radio transceiver.

The term computer-readable medium is used herein to refer to any medium that participates in providing information to processor 802, including instructions for execution. Such a medium may take many forms, including, but not limited to, non-volatile media, volatile media and transmission media. Non-volatile media include, for example, optical or magnetic disks, such as storage device 808. Volatile media include, for example, dynamic memory 804. Transmission media include, for example, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a transmission medium such as a cable or carrier wave, or any other medium from which a computer can read. Information read by a computer from computer-readable media are variations in physical expression of a measurable phenomenon on the computer readable medium. Computer-readable storage medium is a subset of computer-readable medium which excludes transmission media that carry transient man-made signals.

Logic encoded in one or more tangible media includes one or both of processor instructions on a computer-readable storage media and special purpose hardware, such as ASIC 820.

Network link 878 typically provides information communication using transmission media through one or more networks to other devices that use or process the information. For example, network link 878 may provide a connection through local network 880 to a host computer 882 or to equipment 884 operated by an Internet Service Provider (ISP). ISP equipment 884 in turn provides data communication services through the public, world-wide packet-switching communication network of networks now commonly referred to as the Internet 890. A computer called a server host 892 connected to the Internet hosts a process that provides a service in response to information received over the Internet. For example, server host 892 hosts a process that provides information representing video data for presentation at display 814.

In other embodiments, the local network 880 or internet 890 comprise any communication network, which can include one or more wired and/or wireless networks such as a data network (not shown), a wireless network (not shown), a telephony network (not shown), or any combination thereof, each comprised of zero or more nodes. It is contemplated that the data network may be any local area network (LAN), metropolitan area network (MAN), wide area network (WAN), the Internet, or any other suitable packet-switched network, such as a commercially owned, proprietary packet-switched network, e.g., a proprietary cable or fiber-optic network, or any combination thereof. In addition, the wireless network may be, for example, a cellular network and may employ various technologies including code division multiple access (CDMA), wideband code division multiple access (WCDMA), enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, wireless fidelity (WiFi), satellite, and the like. In various embodiments, communication network 105, or portions thereof, can support communication using any protocol, for example, the Internet Protocol (IP).

At least some embodiments of the invention are related to the use of computer system 800 for implementing some or all of the techniques described herein. According to one embodiment of the invention, those techniques are performed by computer system 800 in response to processor 802 executing one or more sequences of one or more processor instructions contained in memory 804. Such instructions, also called computer instructions, software and program code, may be read into memory 804 from another computer-readable medium such as storage device 808 or network link 878. Execution of the sequences of instructions contained in memory 804 causes processor 802 to perform one or more of the method steps described herein. In alternative embodiments, hardware, such as ASIC 820, may be used in place of or in combination with software to implement the invention. Thus, embodiments of the invention are not limited to any specific combination of hardware and software, unless otherwise explicitly stated herein.

The signals transmitted over network link 878 and other networks through communications interface 870, carry information to and from computer system 800. Computer system 800 can send and receive information, including program code, through the networks 880, 890 among others, through network link 878 and communications interface 870. In an example using the Internet 890, a server host 892 transmits program code for a particular application, requested by a message sent from computer 800, through Internet 890, ISP equipment 884, local network 880 and communications interface 870. The received code may be executed by processor 802 as it is received, or may be stored in memory 804 or in storage device 808 or other non-volatile storage for later execution, or both. In this manner, computer system 800 may obtain application program code in the form of signals on a carrier wave.

Various forms of computer readable media may be involved in carrying one or more sequence of instructions or data or both to processor 802 for execution. For example, instructions and data may initially be carried on a magnetic disk of a remote computer such as host 882. The remote computer loads the instructions and data into its dynamic memory and sends the instructions and data over a telephone line using a modem. A modem local to the computer system 800 receives the instructions and data on a telephone line and uses an infra-red transmitter to convert the instructions and data to a signal on an infra-red carrier wave serving as the network link 878. An infrared detector serving as communications interface 870 receives the instructions and data carried in the infrared signal and places information representing the instructions and data onto bus 810. Bus 810 carries the information to memory 804 from which processor 802 retrieves and executes the instructions using some of the data sent with the instructions. The instructions and data received in memory 804 may optionally be stored on storage device 808, either before or after execution by the processor 802.

Figure 9:
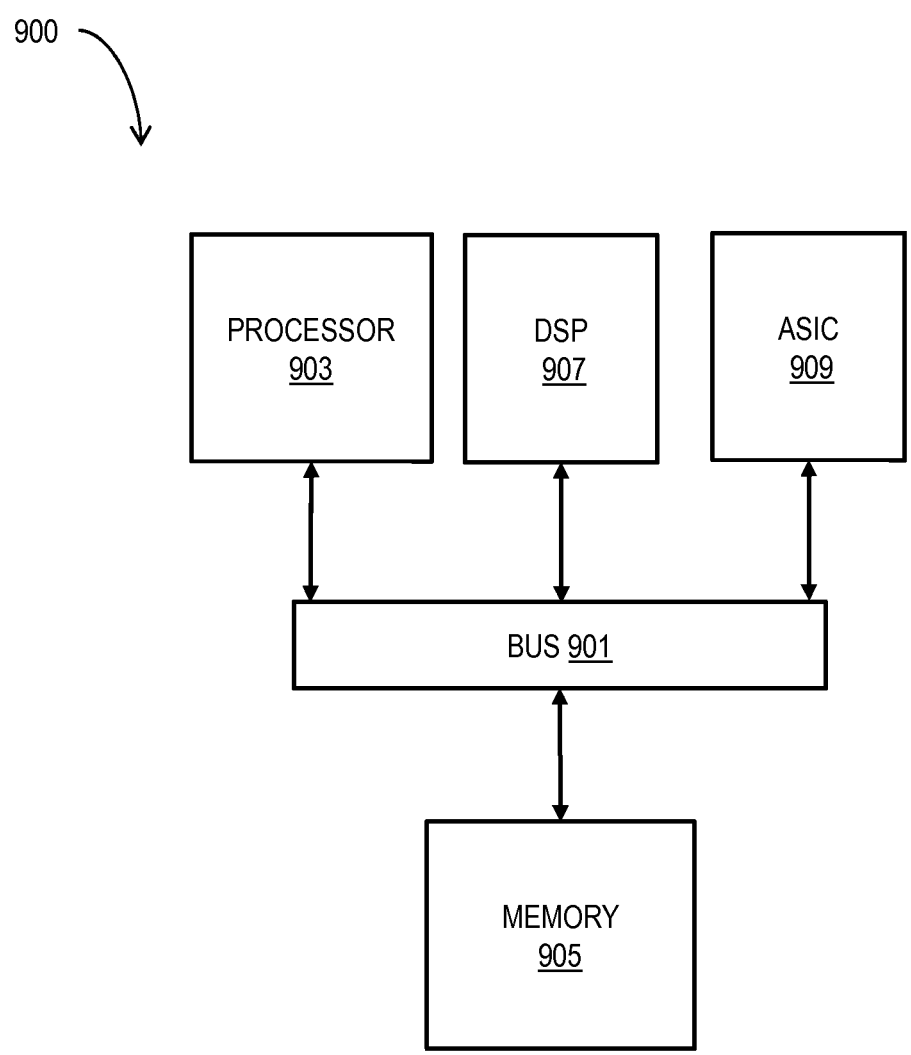
FIG. 9 is a diagram of a chip set that can be used to implement an embodiment of the invention.

FIG. 9 illustrates a chip set 900 upon which an embodiment of the invention may be implemented. Chip set 900 is programmed to carry out the inventive functions described herein and includes, for instance, the processor and memory components described with respect to FIG. 9 incorporated in one or more physical packages. By way of example, a physical package includes an arrangement of one or more materials, components, and/or wires on a structural assembly (e.g., a baseboard) to provide one or more characteristics such as physical strength, conservation of size, and/or limitation of electrical interaction.

In one embodiment, the chip set 900 includes a communication mechanism such as a bus 901 for passing information among the components of the chip set 900. A processor 903 has connectivity to the bus 901 to execute instructions and process information stored in, for example, a memory 905. The processor 903 may include one or more processing cores with each core configured to perform independently. A multi-core processor enables multiprocessing within a single physical package. Examples of a multi-core processor include two, four, eight, or greater numbers of processing cores. Alternatively or in addition, the processor 903 may include one or more microprocessors configured in tandem via the bus 901 to enable independent execution of instructions, pipelining, and multithreading. The processor 903 may also be accompanied with one or more specialized components to perform certain processing functions and tasks such as one or more digital signal processors (DSP) 907, or one or more application-specific integrated circuits (ASIC) 909. A DSP 907 typically is configured to process real-word signals (e.g., sound) in real time independently of the processor 903. Similarly, an ASIC 909 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 903 and accompanying components have connectivity to the memory 905 via the bus 901. The memory 905 includes both dynamic memory (e.g., RAM, magnetic disk, writable optical disk, etc.) and static memory (e.g., ROM, CD-ROM, etc.) for storing executable instructions that when executed perform the inventive steps described herein. The memory 905 also stores the data associated with or generated by the execution of the inventive steps.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:

1. An apparatus comprising:
   a mounting structure;
   an X-ray source mounted to the mounting structure, wherein the X-ray source is configured to produce an X-ray beam that includes photons with photon energy above 1 million electron volts and is configured not to produce an X-ray beam that includes photons with photon energy above six million electron volts; and
   a shield mounted on the mounting structure in opposition to the X-ray source to block the X-ray beam from the X-ray source for photons with photon energies not greater than about six million electron volts.

2. An apparatus as recited in claim 1, wherein the X-ray source excludes a multi-leaf collimator and further comprises at least one shaping cone configured to target at least one sympathetic nerve in a living body.

3. An apparatus as recited in claim 1, further comprising a volume imaging system mounted on the mounting structure in a predetermined relationship to the X-ray source.

4. An apparatus as recited in claim 3, wherein the volume imaging system further comprises a different X-ray source that produces an X-ray frequency with photon energy below about one hundred thousand electron volts.

5. An apparatus as recited in claim 1, further comprising a subject support, wherein the subject support is disposed between the X-ray source and the shield in rotatable orientation relative to the mounting structure.

6. An apparatus as recited in claim 5, wherein the subject support is a chair that supports a subject in a seated position.

7. A method comprising:
   positioning a subject on a support in view of a volume imaging system and an ionizing radiation source;
   collecting volume image data for the subject based on the volume imaging system;
   determining location of a treatment portion of a sympathetic nerve in the subject based at least in part on the volume image data;
   determining movement of the ionizing radiation source to apply a therapeutic radiation dose to the treatment portion of the sympathetic nerve based at least in part on the location of the treatment portion of the sympathetic nerve and relative location of the ionizing radiation source to the volume imaging system; and
   operating the ionizing radiation source to deliver the therapeutic radiation dose to the treatment portion of the sympathetic nerve,
   wherein the ionizing radiation source is an X-ray source that is configured to produce an X-ray beam with photon energy above 1 million electron volts and is configured not to produce an X-ray beam with photon energy above six million electron volts.

8. A method of claim 7, wherein the sympathetic nerve is a renal sympathetic nerve.

9. A method of claim 8, wherein the therapeutic radiation dose is in a range from about 10 gray to about 180 gray.

10. A method of claim 8, wherein the treatment portion of the renal sympathetic nerve is about 0.5 to about 10.0 centimeters long.

11. A method of claim 7, wherein the sympathetic nerve is a thoracic sympathetic nerve.

12. A method of claim 7, wherein the X-ray source is mounted on a mounting structure and a shield is mounted on the mounting structure in opposition to the X-ray source to block the X-ray beam from the X-ray source with photon energies not greater than about six million electron volts.

13. A method of claim 7, wherein the ionizing radiation source is mounted on a mounting structure and the volume imaging system is mounted on the mounting structure in a predetermined relationship to the ionizing radiation source.

14. A method of claim 7, wherein the subject is seated and the movement comprises at least a partial synchronized rotation and revolution in a horizontal plane.

15. A method of claim 14, wherein the movement further comprises at least a partial synchronized rotation and revolution in a plane at a small angle to the horizontal plane.

16. A method of claim 7, wherein both collecting the volume image data and operating the ionizing radiation source to deliver the therapeutic radiation dose are performed before removing or re-positioning the subject.

17. A non-transitory computer-readable medium carrying one or more sequences of one or more instructions which, when executed by one or more processors, cause an apparatus to perform at least the following:
    collect volume image data for a subject based on a volume imaging system;
    determine location of a treatment portion of a sympathetic nerve in the subject based at least in part on the volume image data;
    determine movement of an ionizing radiation source to apply a therapeutic radiation dose to the treatment portion of the sympathetic nerve based at least in part on the location of the treatment portion of the sympathetic nerve and relative location of the ionizing radiation source to the volume imaging system; and
    operate the ionizing radiation source to deliver the therapeutic radiation dose to the treatment portion of the sympathetic nerve;
    wherein the ionizing radiation source is an X-ray source that is configured to produce an X-ray beam with photon energy above 1 million electron volts and is configured not to produce an X-ray beam with photon energy above six million electron volts.

18. A system comprising:
    at least one processor;
    at least one memory including computer program code, the memory and the computer program code configured to, with the processor, cause the apparatus to perform at least the following:
        collect volume image data for a subject based on a volume imaging system;
        determine location of a treatment portion of a sympathetic nerve in the subject based at least in part on the volume image data;
        determine movement of an ionizing radiation source to apply a therapeutic radiation dose to the treatment portion of the sympathetic nerve based at least in part on the location of the treatment portion of the sympathetic nerve and relative location of the ionizing radiation source to the volume imaging system; and
        operate the ionizing radiation source to deliver the therapeutic radiation dose to the treatment portion of the sympathetic nerve;
    a mounting structure;
    an ionizing radiation source mounted to the mounting structure, wherein the ionizing radiation source is configured to produce an X-ray beam with photon energy above 1 million electron volts and is configured not to produce an X-ray beam with photon energy above six million electron volts; and
    a shield mounted on the mounting structure in opposition to the ionizing radiation source to block the X-ray beam from the ionizing radiation source with photon energies not greater than about six million electron volts.

19. An apparatus comprising:
    means for positioning a subject on a support in view of a volume imaging system and an ionizing radiation source;
    means for collecting volume image data for the subject based on the volume imaging system;
    means for determining location of a treatment portion of a sympathetic nerve in the subject based at least in part on the volume image data;
    means for determining movement of the ionizing radiation source to apply a therapeutic radiation dose to the treatment portion of the sympathetic nerve based at least in part on the location of the treatment portion of the sympathetic nerve and relative location of the ionizing radiation source to the volume imaging system; and
    means for operating the ionizing radiation source to deliver the therapeutic radiation dose to the treatment portion of the sympathetic nerve;
    wherein the ionizing radiation source is an X-ray source that is configured to produce an X-ray beam with photon energy above 1 million electron volts and is configured not to produce an X-ray beam with photon energy above six million electron volts.

\* \* \* \* \*